United States Patent [19]

Hartdegen et al.

[11] 4,237,229
[45] * Dec. 2, 1980

[54] IMMOBILIZATION OF BIOLOGICAL MATERIAL WITH POLYURETHANE POLYMERS

[75] Inventors: Frank J. Hartdegen, Columbia; Wayne E. Swann, Pasadena, both of Md.

[73] Assignee: W. R. Grace & Co., New York, N.Y.

[*] Notice: The portion of the term of this patent subsequent to Jun. 13, 1995, has been disclaimed.

[21] Appl. No.: 849,990

[22] Filed: Nov. 9, 1977

Related U.S. Application Data

[60] Division of Ser. No. 644,025, Dec. 24, 1975, abandoned, which is a continuation-in-part of Ser. No. 585,674, Jun. 10, 1975, abandoned.

[51] Int. Cl.² ................................................. C07G 7/02
[52] U.S. Cl. .................................... 435/182; 260/6; 435/180
[58] Field of Search .................. 195/63, 68, DIG. 11; 260/6, 8, 112 R; 424/78, 85, 94; 435/174, 177, 180, 182

[56] References Cited

U.S. PATENT DOCUMENTS

| 3,672,955 | 6/1972 | Stanley | 195/68 |
| 3,905,923 | 9/1975 | Klug | 195/63 X |
| 3,928,138 | 12/1975 | Wood et al. | 195/68 |
| 3,975,350 | 8/1976 | Hudgin et al. | 424/78 X |
| 4,094,744 | 6/1978 | Hartdegen et al. | 195/63 |

FOREIGN PATENT DOCUMENTS 2413137  10/1975  Fed. Rep. of Germany.
953414  3/1964  United Kingdom.

OTHER PUBLICATIONS

Zaborsky O. Immobilized Enzymes, CRC Press, Cleveland, Ohio, 1973, (pp. 145–147).

*Primary Examiner*—David M. Naff
*Attorney, Agent, or Firm*—Philip M. Pippenger

[57] ABSTRACT

A process for immobilizing a biological material which can be a protein, a coenzyme having at least one primary or secondary amino group per molecule, an admixture of said coenzyme and an enzyme which is mediated by said coenzyme, or an antibiotic having at least one primary or secondary amino group per molecule, wherein the biological material is contacted with an excess of an isocyanate-capped liquid polyurethane prepolymer in the absence of water, and the resulting mixture is cured by contacting it with a curing agent to cure the prepolymer and to immobilize the biological material. The resulting mixture can be cured under foam-forming conditions or under nonfoam-forming conditions. The resulting mixture can be formed into a predetermined shape before or during curing or coated onto a surface before or during curing.

73 Claims, 17 Drawing Figures

IMMOBILIZATION OF BIOLOGICAL MATERIAL WITH POLYURETHANE POLYMERS

CROSS-REFERENCE TO RELATED APPLICATIONS

The present application is a divisional of our co-pending application Ser. No. 644,025, filed Dec. 24, 1975, now abandoned, which in turn is a continuation-in-part of Ser. No. 585,674, filed June 10, 1975, now abandoned.

BACKGROUND OF THE INVENTION

1. Field of the Invention

This invention relates to biological material. More particularly, this invention relates to an immobilized biological material (an immobilized biologically active material) having at least one primary or secondary amino group per molecule and to a process for immobilizing such material. Even more particularly, this invention relates to: (a) such biological material which has been immobilized by contact it with an excess of an isocyanate-capped liquid polyurethane prepolymer to form a mixture which is cured by contacting it (the mixture) with an amount of a curing agent (e.g., water or an appropriate amine) effective for curing the biological material; and (b) to the process whereby such biological material is immobilized.

2. Description of the Prior Art

A review of enzyme technology was published in the Aug. 18, 1975 issue of Chemical & Engineering News (pp. 22–41). Chemical & Engineering News is published by the American Chemical Society.

U.S. Pat. No. 3,574,062 (195/63, Sato) teaches a method for preparing a bound protein (an enzyme) wherein a polyester polyurethane is diazotized with a diazonium salt of an amino acid and then coupled with a nonenzymatic animal protein to form a diazotized polyurethane which is reacted with an enzyme to form the immobilized enzyme.

U.S. Pat. No. 3,705,084 (195/63, Reynolds) teaches a flow-through enzyme reactor comprising: (a) a macroporous reactor core; (b) a polymeric surface (which can be a polyurethane resin) on the reactor core; (c) an enzyme adsorbed on the polymeric surface and cross-linked in place thereon by a difunctional agent (e.g., a polyisocyanate).

Reynolds prepares the immobilized enzyme for his reactor by adsorbing an active enzyme on a polymeric surface and further immobilizing the enzyme by cross-linking it in place with a crosslinking agent such as a monomeric polyisocyanate.

German Offenlegungsschrift No. 2,319,706 published Nov. 15, 1973 teaches an enzyme bound to a polyurethane foam and a method for preparing such bound enzyme.

U.S. Pat. No. 3,791,927 (195/63, Forgione et al) teaches a water-insoluble bound protein (enzyme) entrapped within the cells of a self-supporting reticulated cellular material (which can be a polyurethane foam), the protein (enzyme) being bound to the cellular material.

U.S. Pat. No. 3,672,955 (195/68, Stanley) teaches a process for preparing a bound protein (enzyme) comprising: (a) emulsifying an aqueous dispersion of the enzyme with a solution of a polyisocyanate in a volatile water-immiscible solvent (e.g., methylchloroform); (b) admixing the resulting emulsion with a solid particulate carrier; and (c) evaporating the solvent therefrom. Stanley's polyisocyanate can be an isocyanate-capped liquid polyurethane prepolymer. Said U.S. Pat. No. 3,672,955, in its entirety, is incorporated herein by reference.

It is noted that, in his Example 3, Stanley reports the binding of an enzyme component (a peroxidase) of a fermentation broth by admixing a portion of the broth with a polyisocyanate dissolved in methylchloroform. It seems probably that, under Stanley's reaction conditions, any other enzymes which were present in the broth plus any coenzymes which contained a primary or secondary amino group and which were present in the broth would have been immobilized (rendered insoluble).

Silman et al, Annual Review of Biochemistry, 1966, 35 (Part 2), pages 873–908 present a review of methods for preparing water-insoluble derivatives of enzymes, antigens, and antibodies.

Singer, Nature, 1959, 183, 1523–1524 teaches a method for reacting a protein with a diisocyanate (m-xylene diisocyanate).

U.S. patent application Ser. No. 250,012, filed May 3, 1972, and now abandoned (Wood et al, inventors) which is assigned to W. R. Grace & Co. teaches, in Example 21, a foamed polyurethane comprising an immobilized enzyme (urease), a method for preparing such immobilized enzyme, and a method for using it.

Said Application Ser. No. 250,012 also teaches, e. g., in claim 8, a foamable composition comprising: (a) an isocyanate-capped polyurethane prepolymer; (b) water; and (c) biostats, fungicides, or enzymes. A similar teaching occurs in claim 7 of the above-mentioned German Offenlegungsschrift No. 2,319,706.

U.S. patent application Ser. No. 362,488, filed May 21, 1973, and now U.S. Pat. No. 3,928,138 (Wood et al, inventors) which is assigned to W. R. Grace & Co. teaches the preparation of a bound protein (an enzyme) by a process comprising contacting an isocyanate-capped liquid polyurethane prepolymer with an aqueous dispersion of the enzyme under foam-forming conditions, whereby the polyurethane foams and the enzyme becomes integrally bound to the resulting polyurethane foam.

It is noted that, in said Application Ser. No. 362,488, Wood et al report, in their Example 1, that an enzyme (cellulase) present in a fermentation broth was immobilized (bound or rendered insoluble) by admixing the broth with an isocyante-capped liquid polyurethane prepolymer under conditions which produced a foam. It seems probable that, under the conditions of said Example 3, any other enzymes present in the broth plus any coenzymes which contained a primary or secondary amino groups and which were present in the broth would have been immobilized.

Dean et al, U.S. Pat. No. 3,904,478, teach a method for immobilizing coenzymes wherein the coenzyme is immobilized by: (a) forming a thio derivative of the coenzyme in which an amino group of the coenzyme is replaced by a thio group; (b) reacting the thio group with: (i) a bifunctional organic compound having a nucleophilic group so as to couple the bifunctional organic compound to the coenzyme and then coupling the resultant coenzyme reaction product to a water insoluble support material through the unreacted functional group of the bifunctional organic compound; or (ii) a water insoluble support material having a plurality of pendant nucleophilic groups so as to couple the coenzyme to the support material.

Immobilized coenzymes are also taught by: (a) Mosbach et al, Enzyme Eng., 2nd, 1973 (published in 1974) which is abstracted in Chemical Abstracts, 1975, 83, 39185c; (b) McCormick, Methods Enzymol., 1974, 34 (Affinity Tech.; Enzyme Purif., Part B), 300–302, which is abstracted in Chemical Abstracts, 1975, 83, 24325z; (c) Barker, Methods Enzymol., 1974, 34 (Affinity Tech.; Enzyme Purif., Part B), 479–491, which is abstracted in Chemical Abstracts 1975, 83, 39459v; (d) Morse et al, U.S. Pat. No. 3,860,733, which is abstracted in Chemical Abstracts 1975, 82, 138021g; (e) French Pat. No. 2,206,129 (to Merck and Co., Inc.), which is abstracted in Chemical Abstracts 1975, 82, 138024k; (f) Chibata et al, Enzyme Eng., 2nd, 1973 (published 1974), 229–236, which is abstracted in Chemical Abstracts 1975, 83, 39356j; (g) Weibel et al, Enzyme Eng., 2nd, 1973 (published 1974) 203–208, which is abstracted in Chemical Abstracts 1975, 83, 55279s; and (h) Molteni et al, Eur. J. Med. Chem.—Chim. Ther. 1974, 9(6), 618–620, which is abstracted in Chemical Abstracts 1975, 83, 48130h.

U.S. Pat. No. 2,781,339 (260/211.5, Mitz et al) teaches a process for preparing a coenzyme (coenzyme A) comprising admixing a crude aqueous solution of the coenzyme with acid-conditioned charcoal to absorb the coenzyme and thereafter eluting the coenzyme from the charcoal.

Immobilized antibiotics are taught by: (a) Wagman et al, Antimicrob. Agents Chemother, 1975, 7(3), 316–319, which is abstracted in Chemical Abstracts 1975, 83, 22169c; and (b) Seela, Z. Naturforsch., C: Biosci., 1975, 30c (7–8), 544–545, which is abstracted in Chemical Abstracts 1975, 83, 74898j.

U.S. Pat. No. 3,905,923 (260/2.5 AD, Klug) teaches an immobilized enzyme system formed from an enzyme and a hydrophilic poly(urea-urethane) foam, the foam surrounding, entrapping, and supporting the enzyme in an active configuration. The hydrophilic foam is formed by the reaction of water with a hydrophilic isocyanate-capped polyoxyalkylene prepolymer.

Isocyanate-capped polyurethane prepolymers are well known to those skilled in the art. See, for example: (a) the penultimate paragraph on page 854 of Volume 9 of the Second Edition of the Kirk-Othmer "Encyclopedia of Chemical Technology", John Wiley and Sons, Inc., New York, N.Y.; or (b) the third full paragraph in the left hand (first) column of page 872 of the Second Edition of "The Encyclopedia of Chemistry", George L. Clark, Editor, Reinhold Publishing Corporation, New York, N.Y.

It is noted that the cured isocyanate-capped liquid polyurethane prepolymers of our invention (including those comprising immobilized biological materials (i.e., immobilized biologically active materials which are also referred to herein as "immobilized group member(s)") produced by foaming an isocyanate-capped liquid polyurethane prepolymer with water or by the reaction of said prepolymer with water under nonfoaming conditions comprise poly(urea-urethane) products which may be foams, films, discs, tubes, rods, spheres, or the like, and which can be hydrophilic.

SUMMARY OF THE INVENTION

In summary, this invention is directed to a process for immobilizing a biological material (a biologically active material) selected from the group consisting of: (a) a protein; (b) a coenzyme having at least one primary or secondary amino group per molecule; (c) an admixture of said coenzyme and an enzyme which is mediated by said coenzyme; and (d) an antibiotic having at least one primary or secondary amino group per molecule, the process comprising:

A. contacting the group member and an excess of an isocyanate-capped liquid polyurethane prepolymer to form a resulting mixture; and B. curing the resulting mixture by contacting it with an amount of a curing agent effective for immobilizing said biological material under foam-forming or nonfoam-forming conditions, the resulting mixture being shaped before curing where the biological material consists of a protein.

This invention is also directed to the product formed by the aforesaid process.

Any liquid polyurethane prepolymer which contains at least two free isocyanate groups per prepolymer molecule is operable as an immobilizing agent in accordance with this invention. We prefer that the prepolymer contain an average of two isocyanate groups per molecule. An even higher ratio can be used, for example, 2–8 isocyanate groups per polyurethane molecule. Ratios higher than this are operable, but offer no advantage. Any excess isocyanate groups left in the cured polyurethane will be destroyed by hydrolysis upon the first contact with water, for example, during a washing step preliminary to use of the immobilized biologically active material.

DESCRIPTION OF PREFERRED EMBODIMENTS

Figure 1:
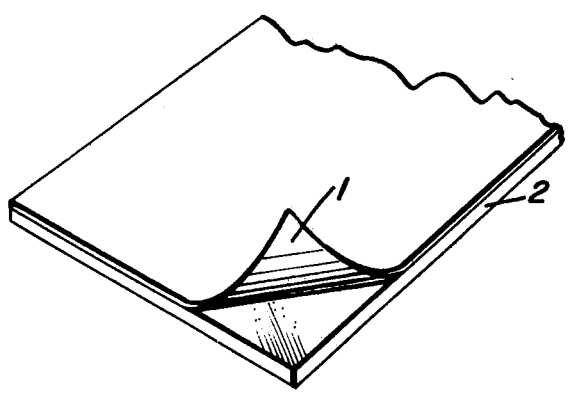
FIG. 1 shows the film of Embodiment C supported on an inert support on which said film was cured.

In one preferred embodiment ("Embodiment A") this invention is directed to a process for immobilizing a biological material selected from the group consisting of: (a) a coenzyme having at least one primary or secondary amino group per molecule; (b) an admixture of said coenzyme and an enzyme which is mediated by said coenzyme; and (c) an antibiotic having at least one primary or secondary amino group per molecule, the process comprising:
   A. contacting the group member and an excess of an isocyanate-capped liquid polyurethane prepolymer to form a resulting mixture; and
   B. curing the resulting mixture by contacting it with an amount of a curing agent effective for immobilizing said biological material.

This invention is also directed to the product formed by the aforesaid process.

In another preferred embodiment ("Embodiment B") this invention is directed to a process for immobilizing a biological material selected from the group consisting of: (a) a protein; (b) a coenzyme having at least one primary or secondary amino group per molecule; (c) an admixture of said coenzyme and an enzyme which is mediated by said coenzyme; and (d) an antibiotic having at least one primary or secondary amino group per molecule, the process comprising:
   A. contacting the group member and an excess of an isocyanate-capped liquid polyurethane prepolymer to form a resulting mixture;
   B. shaping the resulting mixture; and
   C. curing the shaped resulting mixture by contacting it with a curing agent to form a cured shaped article comprising the immobilized biological material.

The shaped article comprising the immobilized biological material (i.e., comprising the group member) can be a film, a disc (which can be prepared by cutting the film, e.g., with a cork bore or stamping apparatus), a tube, a rod, a sphere, or a foam.

This invention is also directed to such shaped article.

The general method for preparing nonfoamed immobilized enzymes recited in the aforesaid Stanley patent (U.S. Pat. No. 3,672,955) can be used to immobilize (bind) the group members of the above Summary, Embodiment A, or Embodiment B in nonfoamed and biologically active form. The particulate solid material (solid carrier) included in Stanley's method can be included or omitted and the product can be a rod, a tube, a self supporting film, a self supporting disc, a sphere, or the like. Stanley's "essentially water-immiscible solvent" can be used or it can be replaced with a water-soluble or substantially water-soluble solvent; a volatile inert solvent is preferred.

In another preferred embodiment ("Embodiment C") this invention is directed to a self supporting cured polyurethane film having two surfaces, said film comprising an immobilized biologically active material selected from the group consisting of:

(a) a protein; (b) a coenzyme having at least one primary or secondary amino group per molecule; (c) an admixture of said coenzyme and an enzyme which is mediated by said coenzyme; and (d) an antibiotic having at least one primary or secondary amino group per molecule.

In another preferred embodiment ("Embodiment D") this invention is directed to a self supporting cured polyurethane disc having two surfaces, said disc comprising an immobilized biologically active material selected from the group consisting of:

(a) a protein; (b) a coenzyme having at least one primary or secondary amino group per molecule; (c) an admixture of said coenzyme and an enzyme which is mediated by said coenzyme; and (d) an antibiotic having at least one primary or secondary amino group per molecule.

In another preferred embodiment ("Embodiment E") this invention is directed to a cured polyurethane tube having an inner surface and an outer surface, said tube comprising an immobilized biologically active material selected from the group consisting of: (a) a protein; (b) a coenzyme having at least one primary or secondary amino group per molecule; (c) an admixture of said coenzyme and an enzyme which is mediated by said coenzyme; and (d) an antibiotic having at least one primary or secondary amino group per molecule.

In another preferred embodiment ("Embodiment F") this invention is directed to a product rod comprising an inert pattern rod having a longitudinal surface and two end surfaces, the longitudinal surface being coated with a cured polyurethane film having an outer longitudinal surface, said film comprising an immobilized biologically active material selected from the group consisting of: (a) a protein; (b) a coenzyme having at least one primary or secondary amino group per molecule; (c) an admixture of said coenzyme and an enzyme which is mediated by said coenzyme; and (d) an antibiotic having at least one primary or secondary amino group per molecule. Separating the pattern rod from the film comprising the immobilized biologically active material (group member) will form the tube of FIG. 5.

Figure 14:
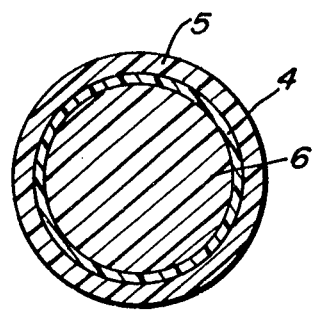
FIG. 14 is a transverse section of the rod of Embodiment G.

In one embodiment of the rod of Embodiment F a second film consisting essentially of cured polyurethane can be bound to the longitudinal surface of the cured film comprising the group member (immobilized biologically active material) to form the rod of FIG. 14. Separating the pattern rod from the film comprising the immobilized group member (biologically active material) will form the tube of FIG. 6.

In another preferred embodiment ("Embodiment G") this invention is directed to a rod comprising an inert pattern rod having a longitudinal surface and two end surfaces, the longitudinal surface being coated with a first film consisting essentially of cured polyurethane, the first film having an outer longitudinal surface, the outer longitudinal surface of the first film being coated with a film of cured polyurethane comprising an immobilized biologically active material selected from the group consisting of: (a) a protein; (b) a coenzyme having at least one primary or secondary amino group per molecule; (c) an admixture of said coenzyme and an enzyme which is mediated by said coenzyme; and (d) an antibiotic having at least one primary or secondary amino group per molecule, the second film being bound to the first film. Separating the pattern rod from the film consisting essentially of cured polyurethane will form the tube of FIG. 7.

In another preferred embodiment ("Embodiment H") this invention is directed to a cured polyurethane sphere comprising an immobilized biologically active material selected from the group consisting of: (a) a protein; (b) a coenzyme having at least one primary or secondary amino group per molecule; (c) an admixture of said coenzyme and an enzyme which is mediated by said coenzyme; and (d) an antibiotic having at least one primary or secondary amino group per molecule.

In another preferred embodiment ("Embodiment I") this invention is directed to a cured self supporting polyurethane foam comprising an immobilized biologically active material selected from the group consisting of:

(a) a coenzyme having at least one primary or secondary amino group per molecule; (b) an admixture of said coenzyme and an enzyme which is mediated by said coenzyme; and (c) an antibiotic having at least one primary or secondary amino group per molecule.

Figure 17:
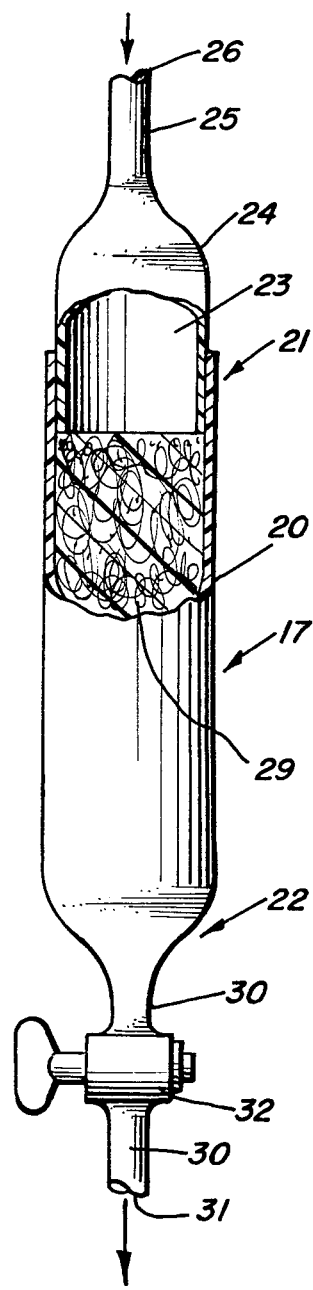
FIG. 17 shows, with parts cut away, a reactor packed with foam comprising the immobilized biologically active material (group member). Said reactor is adapted for utilizing the immobilized biologically active material.

In another preferred embodiment ("Embodiment J") this invention is directed to a reactor comprising:

(a) a column having a lower end and an open upper end;

(b) a cap having an upper portion and an open lower portion, the lower portion of the cap covering and communicating with the open upper end of the column;

(c) an inlet line having an inlet port communicating with the upper portion of the cap;

(d) an outlet line having an outlet port communicating with the lower end of the column; and (e) a cured self supporting polyurethane foam comprising an immobilized biologically active material selected from the group consisting of: (i) a protein; (ii) a coenzyme having at least one primary or secondary amino group per molecule; (iii) an admixture of said coenzyme and an enzyme which is mediated by said coenzyme; and (iv) an antibiotic having at least one primary or secondary amino group per molecule positioned within the column, said foam being produced (foamed) and formed (shaped) in place in the column (i.e., in situ). A value can be inserted in the outlet line as shown in FIG. 17. Said valve can be a stopcock.

In another preferred embodiment ("Embodiment K") this invention is directed to a process for immobilizing a biological material selected from the group consisting of:

(a) an admixture of an enzyme and an antibiotic having at least one primary or secondary amino group per molecule; and (b) an admixture of a coenzyme having at least one primary or secondary amino group per molecule, an enzyme which is mediated by said coenzyme, and an antibiotic having at least one primary or secondary amino group per molecule, the process comprising:

A. contacting the group member and an excess of an isocyanate-capped liquid polyurethane prepolymer to form a resulting mixture; and B. curing the resulting mixture by contacting it with an amount of a curing agent effective for immobilizing said biological material under foam-forming or nonfoam-forming conditions.

This invention is also directed to the product prepared by the process of said embodiment (Embodiment K). Said product can be shaped (e.g., to form a shaped foam, a self supporting film, a self supporting disc, a tube, a rod, or a sphere.

Said product is useful for inhibiting or preventing bacterial decomposition of a material undergoing enzymatic reaction (e.g., to inhibit or prevent bacterial decomposition of sucrose or inert sugar during the hydrolysis of sucrose with invertase to form inert sugar).

DETAILED DESCRIPTION OF THE INVENTION

This invention is in the field of biological materials. More particularly it is in the field of immobilized biological materials including proteins (e.g., enzymes, antibiotics, and antigens), coenzymes having at least one primary or secondary amino group per molecule, and antibiotics having at least one primary or secondary amino group per molecule.

It is an object of this invention to provide a method for immobilizing a biological material selected from the group consisting of:

(a) a protein; (b) a coenzyme having at least one primary or secondary amino group per molecule; (c) an admixture of said coenzyme and an enzyme which is mediated by said coenzyme; and (d) an antibiotic having at least one primary or secondary amino group per molecule without destroying or inactivating the biological activity of the biological material.

It is a further objective of this invention to immobilize such biological material by contacting the biological material with an excess of an isocyanate-capped liquid polyurethane prepolymer to form a resulting mixture and then curing the resulting mixture by contacting it with a curing agent which can be a foam-producing curing agent (i.e., water) or a nonfoam-producing curing agent (e.g., an amine such as aniline, methylamine, diethylamine, or ammonia).

It is a further object of this invention to immobilize the biological material by treating the resulting mixture with water under:

(a) foam-forming; and (b) nonfoam-forming conditions.

It is a further object of this invention to shape the resulting mixture (before curing, during curing, or after curing, or a combination thereof) to produce a shaped object (e.g., a film, a tube, a rod, a disc, a sphere, or the like) comprising the immobilized biological material.

It is a further object of this invention to immobilize a coenzyme and an enzyme which is mediated by the coenzyme to form a product comprising the enzyme and the coenzyme in immobilized and active form.

It is also an object of this invention to immobilize the above-mentioned biological materials in active and reusable form.

The above-mentioned parent application Ser. No. 585,674, filed 10 June 1975, which is not prior art with respect to the instant invention teaches: (a) a process for immobilizing a protein which can be an enzyme, an antibody, or an antigen; and (b) the product of such process, the process comprising admixing the protein and an isocyanate-capped liquid polyurethane prepolymer to form a resulting product and foaming and polymerizing (curing) the resulting product by admixing it with water under foam-forming conditions. The specification of said application Ser. No. 585,674, in its entirety, is incorporated herein by reference.

Chemical Abstracts, 1975, 83, 174745a contains an abstract reporting that Lipatova et al, Ukr. Biokhm. Zh., 1975, 47(4), 532–535 immobilized trypsin on a polyurethane matrix. Said abstract states that:

Two methods were developed for the preparation of trypsin immobilized on a polyurethane matrix. The covalently bound trypsin was prepared by reacting trypsin with toluene diisocyanate and reacting the polyisocyanate obtained with polyoxypropylene glycol, mol. wt. 1500, using 2,4,6-tris(dimethylaminomethyl)-phenol as an accelerator of the reaction. The chem. interaction between trypsin and the polymer was confirmed by ir-spectroscopy and by the decrease in the amt. of free isocyanate groups. The activity of trypsin chem. bound to the polymer was preserved at room temp., for several months. In the free trypsin entrapped in a polymeric net formed by poly(diisocyanate) under conditions in which no chem. interaction between the polymer and enzyme occurred, the activity was also preserved, its value in this case being dependent on the relative content of enzyme in the polymer. It was high when the relative content of the enzyme was low, which might indicate a role for the polymer as a heterogenic catalyst or activator. The proteolytic activity of the polymer with chem. bound trypsin change very little during washing of the column for 24 hrs. with 0.005 M veronal buffer, whereas the polymer with free trypsin under these conditions lost its activity completely. It is believed that the above-discussed Lipatova et al publication is not prior art with respect to the instant invention.

A polyurethane prepolymer is produced in the known way by the reaction of an excess of di- and triisocyanates and other polyisocyanates (including mixtures of polyisocyanates) with compounds containing active hydrogen, particularly glycols, polyglycols, polyester polyols, polyether polyols, other polyols, and mixtures of two or more such polyols. This reaction produces an isocyanate-capped liquid polyurethane prepolymer which can be used in the process of the instant invention.

The above-mentioned U.S. Pat. No. 3,672,955 teaches that proteins (enzymes) can be bound to isocyanate-capped polyurethanes. In the process of said patent the isocyanate-capped polyurethane is dissolved in a water-immiscible solvent. This solution is emulsified, using an emulsifying agent in the presence of an active enzyme which is dispersed in water.

Our process is similar in some respects to that of Stanley's said U.S. Pat. No. 3,672,955. We can use the same isocyanate-capped polyurethane prepolymers (which that patent refers to as polyisocyanates); we can use the same polyols (to prepare our prepolymer); we can use the same enzymes; and we can use the same water-immiscible solvent. As in that patent (although we do not wish to be bound to any particular theory) the mechanism is apparently the reaction of one or more amine and/or hydroxyl groups on the biological material with one or more isocyanate groups on the polyurethane prepolymer molecule.

As used herein the term "liquid isocyanate-capped polyurethane prepolymer" means a liquid polyurethane or polyurea molecule containing at least about two free isocyanate groups per molecule.

Representative examples of polyisocyanates which can be reacted with an active hydrogen containing compound (e.g., a glycol, polyol, polyglycol, polyester polyol, polyether polyol, and the like) to make an isocyanate-capped polyurethane in accordance with the invention include:

toluene-2,4-diisocyanate
toluene-2,6-diisocyanate
commercial mixtures of toluene-2,4- and 2,6-diisocyanates
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
4,4'-biphenylene diisocyanate
3,3'-dichloro-4,4'-biphenylene diisocyanate
1,6-hexamethylenediisocyanate
1,4-tetramethylene-diisocyanate
1,10-decamethylenediisocyanate
1,5-naphthalenediisocyanate
cumene-2,4-diisocyanate
4-methoxy-1,3-phenylenediisocyanate
4-chloro-1,3-phenylenediisocyanate
4-bromo-1,3-phenylenediisocyanate
4-ethoxy-1,3-phenylenediisocyanate
2,4'-diisocyanatodiphenylether
5,6-dimethyl-1,3-phenylenediisocyanate
2,4-dimethyl-1,3 phenylenediisocyanate
4,4'-diisocyanatodiphenylether
benzidinediisocyanate
4,6-dimethyl-1,3-phenylenediisocyanate
9,10-anthracenediisocyanate
4,4'-diisocyanatodibenzyl
3,3'-dimethyl-4,4'-diisocyanatodiphenylmethane
2,6-dimethyl-4,4'-diisocyanatodiphenyl
2,4-diisocyanatostilbene
3,3'-dimethyl-4,4'-diisocyanatodiphenyl
3,3'-dimethoxy-4,4'-diisocyanatodiphenyl
1,4-anthracenediisocyanate
2,5-fluorenediisocyanate
1,8-naphthalenediisocyanate
2,6-diisocyanatobenzfuran
2,4,6-toluenetriisocyanate, and
p,p',p"-triphenylmethane triisocyanate.

A useful class of liquid isocyanate-capped polyurethane prepolymers are those derived from polyether polyols and polyester polyols. These compounds may be prepared, as is well known in the art, by reacting a polyether (or polyester) polyol with a polyisocyanate, using an excess of the latter to ensure provision of free isocyanate groups in the product. A typical, but by no means limiting, example is illustrated in idealized equation form below:

HO—(CH₂—CH₂—CH₂—CH₂—O—)ₘ H   Polyether polyol

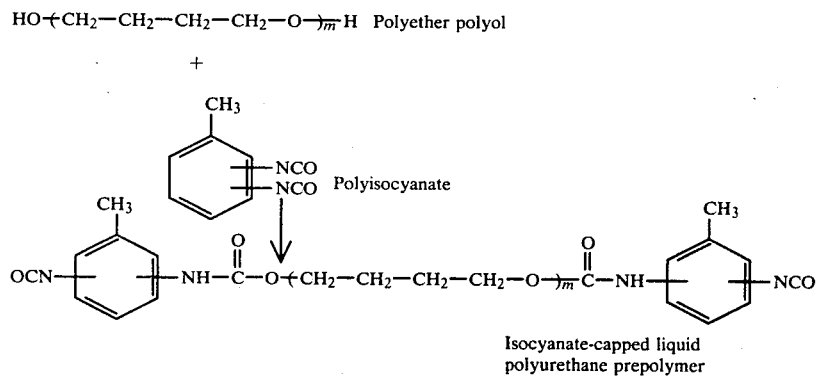

Isocyanate-capped liquid polyurethane prepolymer (In the above formulas, m represents the number of tetramethyleneether repeating units. This may range, for example, about from 5 to 50.)

The compounds useful for the purposes of the invention may be prepared by reacting any of the above-exemplified polyisocyanates with any of a wide variety of polyether polyols and polyester polyols, and representative examples of these polyols are described below.

Among the polyether polyols which may be so used are those prepared by reaction of an alkylene oxide with an initiator containing active hydrogen groups, a typical example of the initiator being a polyhydric alcohol such as ethylene glycol; a polyamine such as ethylene diamine; phosphoric acid, etc. The reaction is usually carried out in the presence of either an acidic or basic catalyst. Examples of alkylene oxides which may be employed in the synthesis include ethylene oxide, propylene oxide, any of the isomeric butylene oxides, and mixtures of two or more different alkylene oxides such as mixtures of ethylene and propylene oxides. The resulting polyether polyols contain a polyether backbone and are terminated by hydroxyl groups. The number of hydroxyl groups per polymer molecule is determined by the functionality of the active hydrogen initiator. For example, a difunctional alcohol such as ethylene glycol (as the active hydrogen initiator) leads to polyether chains in which there are two hydroxyl groups per polymer molecule. When polymerization of the oxide is carried out in the presence of glycerol, a trifunctional alcohol, the resulting polyether molecules contain an average of three hydroxyl groups per molecule. Even higher functionality—more hydroxyl groups—is obtained when the oxide is polymerized in the presence of such polyols as pentaerythritol, sorbitol, sucrose dipentaerythritol, and the like. In addition to those listed above, other examples of polyhydric alcohols which may be reacted with alkylene oxides to produce useful polyether polyols include:
propylene glycol
trimethylene glycol
1,2-butylene glycol
1,3-butanediol
1,4-butanediol
1,5-pentanediol
1,2-hexylene glycol
1,10-decanediol
1,2-cyclohexanediol
2-butene-1,4-diol
3-cyclohexene-1,1-dimethanol
4-methyl-3-cyclohexene-1,1-dimethanol
3-methylene-1,5-pentanediol
diethylene glycol
(2-hydroxyethoxy)-1-propanol
4-(2-hydroxyethoxy)-1-butanol
5-(2-hydroxypropoxy)-1-pentanol
1-(2-hydroxymethoxy)-2-hexanol
1-(2-hydroxypropoxy)-2-octanol
3-allyloxy-1,5-pentanediol
2-allyloxymethyl-2-methyl-1,3-propanediol
[(4-pentyloxy)methyl]-1,3-propanediol
3-(o-propenylphenoxy)-1,2-propanediol
thiodiglycol
2,2'-[thiobis(ethyleneoxy)]diethanol
polyethyleneether glycol (molecular weight about 200)
2,2'-isopropylidenebis(p-phenyleneoxy)dietharol
1,2,6-hexanetriol
1,1,1-trimethylolpropane
3-(2-hydroxyethoxy)-1,2-propanediol
3-(2-hydroxypropoxy)-1,2-propanediol
2,4-dimethyl-2-(2-hydroxyethoxy)methylpentanediol-1,5
1,1,1-tris[(2-hydroxyethoxy)methyl]ethane
1,1,1-tris[(2-hydroxypropoxy)methyl]propane
triethanolamine
triisopropanolamine
resorcinol
pyrogallol
phloroglucinol
hydroquinone
4,6-di-tertiarybutyl catechol
catechol
orcinol
methylphloroglucinol
hexylresorcinol
3-hydroxy-2-naphthol
2-hydroxy-1-naphthol
2,5-dihydroxy-1-naphthol
bis-phenols such as 2,2-bis(p-hydroxyphenyl)propane and bis-(p-hydroxyphenyl)methane
1,1,2-tris-(hydroxyphenyl)ethane
1,1,3-tris-(hydroxyphenyl)propane.

An especially useful category of polyether polyols are the polytetramethylene glycols. They are prepared by the ring-opening polymerization of tetrahydrofuran, and contain the repeating unit.

—CH₂—CH₂—CH₂—CH₂—O— in the polymer backbone. Termination of the polymer chains is by hydroxyl groups.

Also especially desirable are the polyoxyethylene polyols HO—(CH₂CH₂—O)ₓH in which x is an average number such that the polyol has an average molecular weight of up to about 1000 (or about 2000 or somewhat higher).

The polyester polyols which may be employed as precursors are most readily prepared by condensation polymerization of a polyol with a polybasic acid. The polyol and acid reactants are used in such proportions that essentially all the acid groups are esterified and the resulting chain of ester units is terminated by hydroxyl groups. Representative examples of polybasic acids for producing these polymers are oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, α-hydromuconic acid, β-hydromuconic acid, α-butyl-α-ethylglutaric acid, α,β-diethylsuccinic acid, o-phthalic acid, isophthalic acid, terephthalic acid, hemimellitic acid, trimellitic acid, trimesic acid, mellophanic acid, prehnitic acid, pyromellitic acid, citric acid, benzenepentacarbosylic acid, 1,4-cyclohexane dicarboxylic acid, diglycollic acid, thiodiglycollic acid, dimerized oleic acid, dimerized linoleic acid, and the like. Representative examples of polyols for forming these polymers include ethylene glycol, 1,3-propylene glycol, 1,2-propylene glycol, 1,4-butylene glycol, 1,3-butylene glycol, 1,2-butylene glycol, butene-1,4 diol, 1,5-pentane diol, 1,4-pentane diol, 1,3-pentane diol, 1,6-hexane diol, hexane-1,6-diol, 1,7-heptane diol, diethylene glycol, glycerine, trimethylol propane, 1,3,6-hexanetriol, trimetholamine, pentaerythritol, sorbitol, and any of the other polyols listed hereinabove in connection with the preparation of polyether polyols.

It is believed that, on being intimately contacted with a protein (or other biological material containing at least one primary or secondary amino group per molecule) such as an enzyme, antibody, antigen, or the like, an isocyanate-capped polyurethane prepolymer becomes chemically very active. Some of its free isocyanate groups of the prepolymer react with the amine groups of the material, and subsequently when water is present, some isocyanate groups react with water to give carbon dioxide and to form amine groups which react with free isocyanate groups of polyurethane molecules to form urea type links. These latter amine groups may react with free isocyanate groups on neighboring polyurethane molecules, and this reaction (by forming a urea linkage) will cause further growth of the polyurethane molecule and may also introduce cross links between the polyurethane molecules. This further preliminary growth and cross linking is essential for the formation of a good polyurethane foam.

Other additives such as crosslinking agents (polyamines, polythiols, polyacids) surfactants, wetting agents, antifoaming agents, dyes, antioxidants, fillers, etc., may also be present during the curing and immobilization step.

It is, of course, the release of the carbon dioxide that provides gas for foam formation where working under foam-forming conditions.

The ratio of biological material to isocyanate-capped liquid polyurethane prepolymer is not critical. However it is important that said ratio be such that all of the isocyanate groups of the prepolymer are not consumed by reaction with the protein, thereby to leave unreacted isocyanate groups available to react with curing agent to cure the above-defined resulting mixture and to immobilize the biological material (the group member of the above Summary which is also called a "biologically active material").

Where working under foam-forming conditions the ratio of water to group member plus isocyanate-capped liquid polyurethane prepolymer is not critical; however, we generally prefer to use about 0.5–3 or 0.9–2 parts by weight of water per part by weight of said prepolymer plus group member.

Where using water as curing agent under nonfoaming conditions we generally prefer to use about a stoichiometric amount of water.

Where using an amine as curing agent we generally prefer to use at least about a stoichiometric amount of amine. Amine curing agents do not produce foaming.

It is preferred that sufficient curing agent (whether water or amine and whether under foaming or nonfoaming conditions) be used to react with most (or all) of the free isocyanates present on the prepolymer. However, the final product can be wasted with water to "inactivate" (react with) any free isocyanate groups on the final product before using.

In the process and product of this invention:

1. The isocyanate-capped liquid polyurethane prepolymer is prepared by reacting toluene diisocyanate and a polyethylene glycol.

2. The isocyanate-capped liquid polyurethane prepolymer is prepared by reacting toluene diisocyanate and a polyethylene glycol having a molecular weight of about 800–1,200.

3. The isocyanate-capped liquid polyurethane prepolymer is prepared by reacting toluene diisocyanate and a member selected from the group consisting of a polyoxybutylene polyol polymer, ethylene glycol, diethylene glycol, a polyoxyethylene polyol polymer, pentaerythritol, glycerol, trimethylolpropane, and a polyoxypropylene polyol polymer.

4. The isocyanate-capped liquid polyurethane prepolymer is prepared by reacting toluene diisocyanate with an admixture of a polyethylene glycol having a molecular weight of about 800–1,200 and trimethylolpropane, the trimethylolpropane and the polyethylene glycol being provided in a mole ratio of about 1:1–4 and the toluene diisocyanate being provided at a rate of about 0.85–1.25 mole per equivalent of —OH provided by the polyethylene glycol plus the trimethylolpropane.

5. The cured product (the product or article formed by curing the isocyanate) which comprises the immobilized group member is washed to remove nonimmobilized group member and to hydrolyze any unreacted isocyanate groups.

6. The isocyanate-capped liquid polyurethane prepolymer and the group member are admixed to form an intermediate product which is cured and foamed by admixing it with an amount of water effective for curing and foaming the intermediate product.

7. An aqueous solution of the group member and the isocyanate-capped liquid polyurethane prepolymer are contacted prior to a subsequent foaming step under foam-forming conditions whereby the polyurethane foams and the group member becomes immobilized.

8. The group member is a coenzyme having at least one primary or secondary amino group per molecule, e.g.,:

nicotinamide-adenine dinucleotide,
nicotinamide-adenine dinucleotide phosphate,
flavin mononucleotide,
adenosine triphosphate,
flavin adenine dinucleotide, and thiamin pyrophosphate.

9. The group member is an admixture of a coenzyme having at least one primary or secondary amino group per molecule and an enzyme which is mediated by the coenzyme; the following are illustrations thereof:

(a) the coenzyme is nicotinamide-adenine dinucleotide and the enzyme is
   alcohol dehydrogenase,
   isocitric dehydrogenase,
   α-glycerolphosphate dehydrogenase,
   lactic dehydrogenase, or,
   glyceraldehyde-3-phosphate dehydrogenase;

(b) the coenzyme is nicotinamide-adenine dinucleotide phosphate and the enzyme is
   malic enzyme,
   glucose-6-phosphate dehydrogenase,
   5-dehydroshikimic reductase, or
   glutathione reductase;

(c) the coenzyme is flavin mononucleotide and the enzyme is
   glycolic acid oxidase,
   yeast cytochrome c reductase,
   luciferase, or
   nitro reductase;

(d) the coenzyme is adenosine triphosphate and the enzyme is
   glutamyl transferase,
   glutathione synthetase,
   glycocyamine phosphokinase,
   hippuric acid synthetase, or
   luciferase;

(e) the coenzyme is flavin adenine dinucleotide and the enzyme is
   D-amino acid oxidase,
   aldehyde oxidase,
   succinic dehydrogenase,
   nitrate reductase,
   xanthine oxidase,
   lipoyl dehydrogenase,
   diaphorase,
   flavin peroxidase, or
   glycine oxidase; or (f) the coenzyme is thiamin pyrophosphate and the enzyme is
   carboxylase,
   α-keto acid dehydrogenase, or
   transketolase.

10. The group member is an antibiotic having at least one primary or secondary amino group per molecule; the following are examples of such antibiotics:
   ampicillin,
   bacitracin,
   colistin, and
   neomycin.

11. The curing agent can be in liquid or vapor form and it can be "neat" (undiluted) or it can be diluted with a solvent where in the liquid state or with a gas where in the vapor state. Typical curing agents include water or an amine having zero to about 10 carbon atoms per molecule. Typical examples of such amine are

| | |
|---|---|
| ammonia, | toluidine, |
| hydroxylamine, | diethylamine, |
| hydrazine, | methylaniline, |
| diethylenetriamine | dimethylamine, |
| propylamine, | propylamine, |
| butylamine, | dipropylamine, |
| ethylenediamine, | dibutylamine, |
| aniline, | and the like. |

Typical examples of inert gases useful for diluting the curing agent where it is in the vapor state include air, oxygen, nitrogen, hydrogen, carbon dioxide, methane, argon, helium, xenon, and the like.

Typical examples of inert solvents useful for diluting the curing agent are water (where the curing agent is an amine), acetone, methyl ethyl ketone, methyl alcohol, ethyl alcohol, a propyl alcohol, a butyl alcohol, dimethylformamide, dimethyl sulfoxide, N-methyl-2-pyrrolidone, methylchloroform, benzene, toluene, xylene, carbon tetrachloride, chloroform, hexane, petroleum ether, and the like.

12. The group member is immobilized by a process in which:

(a) the isocyanate-capped liquid polyurethane prepolymer and the group member are admixed to form an intermediate product; and (b) the intermediate product is cured and foamed by admixing it with an amount of water effective for curing and foaming the intermediate product.

13. The group member is immobilized by a process in which an aqueous solution of the group member and the isocyanate-capped liquid polyurethane prepolymer are contacted prior to a subsequent foaming step under foam-forming conditions whereby the polyurethane foams and the group member becomes immobilized.

14. The resulting mixture (i.e. mixture of prepolymer + group member) can be cured under foam-forming (foaming) or nonfoam-forming (i.e. nonfoaming) conditions.

15. The curing agent can be water or an amine having 0–10 carbon atoms per molecule and at least one primary or secondary amino group per molecule.

16. The resulting mixture can be cured under nonfoam-forming conditions in which:

(a) the resulting mixture is admixed with an inert volatile solvent and water to form an aqueous system; and (b) volatile components are evaporated from the aqueous system.

The volatile solvent can be water soluble in which case the aqueous system is a solution, or the volatile solvent can be essentially water insoluble in which case the aqueous system is an emulsion. The aqueous system can be admixed with a solid carrier in particulate form before evaporating volatile components therefrom. Operable solvents include acetone, methyl ethyl ketone, methyl alcohol, ethyl alcohol, a propyl alcohol, a butyl alcohol, dimethylformamide, dimethyl sulfoxide, N-methyl-2-pyrrolidone, methylchloroform, benzene, toluene, xylene, carbon tetrachloride, chloroform, hexane, petroleum ether, and the like.

17. The group member can be immobilized under nonfoam-forming conditions by admixing an aqueous solution of the group member with an inert volatile solvent to form an aqueous system and mixing the aqueous system with an excess of the isocyanate-capped liquid polyurethane prepolymer to immobilize the group member. Where the inert volatile solvent is water soluble the aqueous system is a solution and where said solvent is essentially or substantially insoluble in water the aqueous system is an emulsion. Operable solvents include but are not limited to acetone, methyl ethyl ketone, methyl alcohol, ethyl alcohol, a propyl alcohol, a butyl alcohol, dimethylformamide, dimethyl sulfoxide, N-methyl-2-pyrrolidone, methylchloroform, benzene, toluene, xylene, carbon tetrachloride, chloroform, hexane, petroleum ether, and the like.

18. The protein can be:
(a) an enzyme, e.g.:
urease,
trypsin,
lactase,
glucose oxidase,
chymotrypsin,
ribonuclease,
peroxidase,
pepsin,
rennin,
invertase,
papain,
asparaginase,
pectinase,
pectin esterase,
penicillin amidase,
glucose isomerase,
lysozyme,
amino acid acylase,
pronase,
alcohol dehydrogenase,
α-amylase,
β-amylase,
subtilisin,
amino acid oxidase,
catalase,
tannase,
phenol oxidase,
glucoamylase,
pullulanase,
cellulase,
ficin,
bromelain,
pancreatin,
isoamylase,
lipase,
malic dehydrogenase,
hexokinase,
lactate dehydrogenase,
adenosine deaminase,
uricase,
galactose oxidase,
diaphorase,
cholinesterase,
aldolase,
pyruvate carboxylase,
phospharylase,
cephalosporin amidase,
isocitric dehydrogenase,
α-glycerolphosphate dehydrogenase,
glyceraldehyde-3-phosphate dehydrogenase,
malic enzyme,
glucose-6-phosphate dehydrogenase,
5-dehydroshikimic reductase,
glutathione reductase,
glycolic acid oxidase,
yeast cytochrome c reductase,
luciferase,
nitrite reductase
glutamyl transferase,
glutathione synthetase,
glycocyamine phosphokinase,
hippuric acid synthetase,
aldehyde oxidase,
succinic dehydrogenase,
nitrate reductase,
xanthine oxidase,
lipoyl dehydrogenase,
flavin peroxidase,
glycine oxidase,
carboxylase,
α-keto acid dehydrogenase, or
transketolase;
(b) an antibody, e.g.: human immunoglobulin G or hepatitis antibody; or
(c) an antigen, e.g.: rheumatoid arthritis factor.

19. The article produced (product) can be a film comprising the immobilized group member. Said film can be prepared by a process in which:
(a) the resulting mixture is applied to an inert solid surface and spread thereon to form a film of the resulting mixture supported on the inert solid surface; and
(b) the film of resulting mixture is cured by exposing it to an amount of the curing agent effective for curing the resulting mixture and immobilizing the group member.

The film can be stripped from the support (inert solid surface), and if desired cut into discs.

If desired, a second film of the resulting mixture can be applied to the cured film and cured thereon and bonded thereto by exposing the second film to an amount of the curing agent effective for curing the resulting mixture and immobilizing the group member to increase the thickness and strength of the cured film.

Also, if desired, a film of isocyanate-capped liquid polyurethane prepolymer can be applied to the cured film and cured thereon and bonded thereto (i.e., bound thereto) by exposing the film of isocyanate-capped liquid polyurethane prepolymer to an amount of the curing agent effective for curing the film of isocyanate-capped liquid polyurethane prepolymer to strengthen the film of immobilized group member. The resulting film can be stripped from the support to yield a first laminate film comprising a film of immobilized group member bound (bonded) to a film of cured polyurethane prepolymer which can be designated "Film A". A fully equivalent film can be prepared by applying a film of the isocyanate-capped liquid polyurethane prepolymer to the support surface, curing the prepolymer film, applying a film of the resulting mixture to the film of cured prepolymer, curing the film of resulting mixture to form a second laminate film comprising a film of immobilized group member bound to the film of cured prepolymer. Stripping the second laminate film from the support produces a film which can be designated "Film B". Films A and B are fully equivalent and the procedures by which they are made are fully equivalent.

The inert solid surface used to prepare films comprising the immobilized group member can be any smooth inert solid surface. Examples of such surfaces are polymeric (plastic) surfaces (e.g., polyolefin—including polyethylene and polypropylene surfaces—Teflon surfaces, nylon surfaces, polyvinyl chloride surfaces, polyvinyl acetate surfaces, polyacrylonitrile surfaces, polystyrene surfaces, and the like), glass surfaces, concrete surfaces, stone surfaces, ceramic surfaces, metal surfaces (e.g., stainless steel surfaces, mild steel surfaces, aluminum surfaces, zinc surfaces, copper surfaces, nickel surfaces, chrome surfaces), rubber surfaces, and the like.

20. The resulting mixture and/or the isocyanate-capped liquid polyurethane prepolymer can be diluted with an inert volatile solvent which can be a water soluble solvent or a solvent which is immiscible or substantially immiscible in water. Typical solvents which can be used for this purpose include acetone, methyl ethyl ketone, methyl alcohol, ethyl alcohol, a propyl alcohol, a butyl alcohol, dimethylformamide, dimethyl sulfoxide, N-methyl-2-pyrrolidone, methylchloroform, benzene, toluene, xylene, carbon tetrachloride, chloroform, hexane, petroleum ether, and the like.

21. The product (article produced) can be a tube comprising the immobilized group member. Said tube can be prepared by a process in which (a) the resulting mixture is applied to the inner surface of a pattern tube having an inner surface and an outer surface to form a film of the resulting mixture on the inner surface of the pattern tube; and (b) the film of resulting mixture is cured by exposing it to an amount of the curing agent effective for curing the resulting mixture and immobilizing the group member to form the cured tube comprising the immobilized group member, the cured tube having an inner surface and an outer surface.

The tube comprising the immobilized group member can be separated from the pattern tube, e.g., by breaking the pattern tube if it (the pattern tube) is made of glass, or by slipping the tube comprising the immobilized group member from the pattern tube.

If desired, a second film of resulting mixture can be applied to the inner surface of the cured tube comprising the immobilized group member and cured thereon and bonded thereto by exposing the second film to an amount of the curing agent effective for curing the resulting mixture and immobilizing the group member to increase the thickness and strength of the tube comprising the immobilized group member.

Also, if desired, a film of isocyanate-capped liquid polyurethane prepolymer can be applied to the inner surface of cured tube comprising the immobilized group member and cured thereon and bonded thereto by exposing the film of isocyanate-capped liquid polyurethane prepolymer to an amount of the curing agent effective for curing the prepolymer to increase the strength of the tube comprising the immobilized group member.

22. The product can be a tube comprising the immobilized group member. It can be prepared by a process in which:

(a) the isocyanate-capped liquid polyurethane is applied to the inner surface of a first tube which is a pattern tube having an inner surface and an outer surface to form a film of the isocyanate-capped liquid polyurethane prepolymer on the inner surface of the first tube;

(b) the film of isocyanate-capped liquid polyurethane prepolymer is cured by exposing it to an amount of the curing agent effective for curing the prepolymer to form a second tube comprising cured prepolymer, the second tube having an inner surface and an outer surface;

(c) the resulting mixture is applied to the inner surface of the second tube to form a film of the resulting mixture on the inner surface of the second tube; and (d) the film of resulting mixture is cured and bonded to the inner surface of the second tube by exposing the film of resulting mixture to an amount of the curing agent effective for curing the resulting mixture and immobilizing the group member to form a third tube comprising the immobilized group member bonded to the inner surface of the second tube.

The third tube can be separated from the pattern tube.

The pattern tube (which can be a pipe) used to prepare tubes comprising the immobilized group member can be a tube of any inert material. Typical examples of such inert materials are polymers (plastics) such as polyolefins—including polyethylene and polypropylene—Teflon, nylon, polyvinyl chloride, polyvinyl acetate, polyacrylonitrile, polystyrene, and the like, glass, ceramic materials, metals (e.g., stainless steel, mild steel, copper, aluminum, zinc, nickel, and tin), rubber, and the like.

23. The product can be a rod comprising the immobilized group member. Such product rod can be prepared by a process in which:

(a) the resulting mixture is applied to the longitudinal surface of a pattern rod having a longitudinal surface and two end surfaces to form a film of the resulting mixture on the longitudinal surface; and (b) the film of resulting mixture is cured by exposing it to an amount of the curing agent effective for curing the resulting mixture and immobilizing the group member to form a product rod comprising the pattern rod having on its longitudinal surface a coating comprising the immobilized group member.

If desired, the coating comprising the immobilized group member can be separated from the pattern rod, e.g., by breaking the pattern rod if it is made of glass, or by slipping said coating off the pattern rod to produce a tube comprising the immobilized group member.

If desired, a second film of the resulting mixture can be applied to the coating comprising the immobilized group member and cured thereon and bonded thereto by exposing the second film to an amount of curing agent effective for curing the resulting mixture and immobilizing the group member to strengthen and increase the thickness of the coating comprising the immobilized group member.

Also, if desired, a film of the isocyanate-capped liquid polyurethane prepolymer can be applied to the coating comprising the immobilized group member and cured thereon and bonded thereto by exposing the film of isocyanate-capped liquid polyurethane prepolymer to an amount of curing agent effective for curing the isocyanate-capped liquid polyurethane prepolymer to strengthen the coating comprising the immobilized group member.

If desired, the coating comprising the immobilized group member with the cured prepolymer bound thereto or the coating comprising two layers of immobilized group member (i.e., two layers of resulting mixture) can be separated from the pattern rod to form a tube having an inner surface comprising the immobilized group member and an outer surface comprising the cured prepolymer or the immobilized group member, respectively.

24. The product can be a product rod comprising the immobilized group member prepared by a process in which:

(a) the isocyanate-capped liquid polyurethane prepolymer is applied to a pattern rod having a longitudinal surface and two end surfaces to form a film of isocyanate-capped liquid polyurethane prepolymer on the longitudinal surface;

(b) the film of isocyanate-capped liquid polyurethane prepolymer is cured by exposing it to an amount of the curing agent effective for curing the isocyanate-capped liquid polyurethane prepolymer to form an intermediate rod comprising the pattern rod having on its longitudinal surface a first coating of cured prepolymer, the first coating having an inner surface adjacent to the longitudinal surface of the pattern rod and an outer surface; and (c) a film of resulting mixture is applied to the outer surface of the first coating and cured thereon and bonded thereto by exposing the film of resulting mixture to an amount of the curing agent effective for curing the resulting mixture and immobilizing the group member to form a product rod comprising the pattern rod with a final coating thereon, the final coating comprising the first coating with the second coating bound thereto.

The product can be a tube comprising the immobilized group member prepared by separating the final coating from the pattern rod to form said tube.

The pattern rod used to prepare rods comprising the immobilized group member can be a rod or bar of any inert material. Typical examples of such inert material are polymers (plastics) such as polyolefins—including polyethylene and polypropylene—Teflon, nylon, polyvinyl chloride, polyvinyl acetate, polyacrylonitrile, polystyrene, and the like, glass, ceramic materials, metals (e.g., stainless steel, mild steel, copper, and aluminum), rubber, and the like. The rod can be hollow, e.g., it can be a tube or pipe with or without capped ends or with one end capped.

25. The product can be a sphere prepared by a process in which the sphere is formed and cured by feeding the resulting mixture dropwise into a fluid comprising the curing agent and permitting the resulting spherical drop to fall freely through the fluid. The fluid can be a liquid or a vapor, and it (the fluid) can: (a) consist of the curing agent; or (b) consist essentially of the curing agent dissolved in an inert volatile solvent (where the fluid is a liquid); or (c) consist essentially of the curing agent and an inert gas (where the fluid is a vapor (or gas)). If desired, the resulting mixture can be diluted with an inert volatile solvent to form a solution which is fed dropwise into the fluid comprising the curing agent; where this is done the inert volatile solvent can be vaporized while curing the resulting mixture.

The drawings illustrate certain embodiments of the instant invention.

FIG. 1 shows self supporting cured polyurethane film 1 comprising immobilized biologically active material (i.e., comprising the immobilized group member of the above Summary) supported on inert solid surface 2 (a smooth surface).

Figure 2:
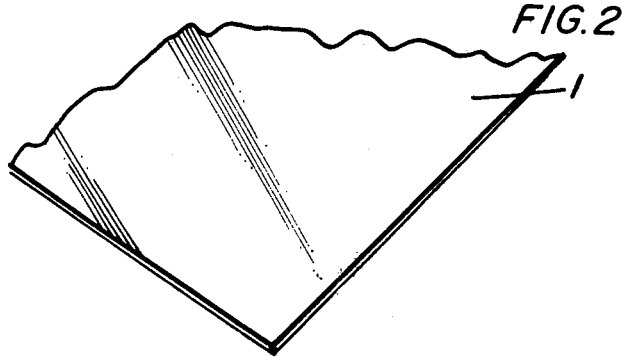
FIG. 2 shows the film of Embodiment C after the film has been stripped from the support.

FIG. 2 shows said film 1 after it (film 1) has been stripped (separated) from said inert surface.

Figure 3:
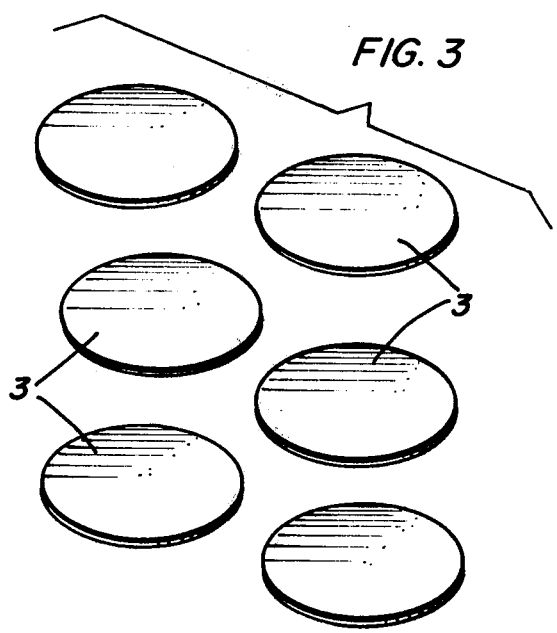
FIG. 3 shows the discs of Embodiment D.

FIG. 3 shows self supporting discs 3 made of cured polyurethane (cured polyurethane prepolymer) comprising the immobilized biologically active material.

Figure 4:
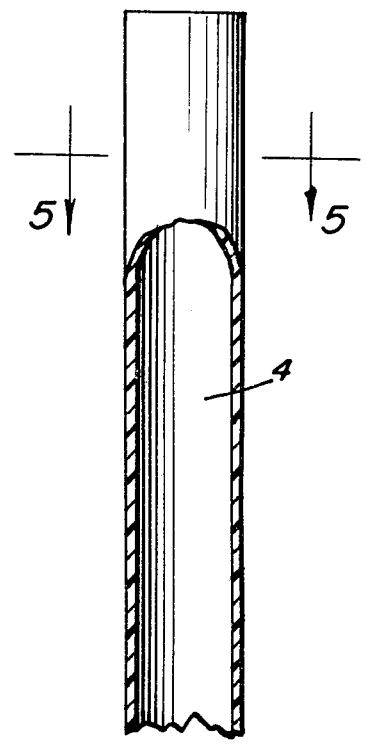
FIG. 4 is a lateral view of the tube of Embodiment E with a part cut away.

FIG. 4 shows a tube made of cured polyurethane comprising immobilized biologically active material 4.

Figure 5:
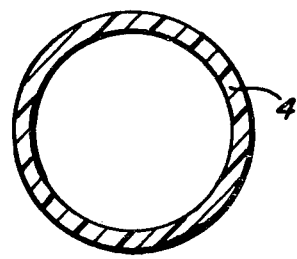
FIG. 5 is a transverse section of the tube of Embodiment E taken along line 5—5 of FIG. 4.

FIG. 5 shows a transverse section of the tube of FIG. 4, said tube being made of cured polyurethane comprising immobilized biologically active material 4.

Figure 6:
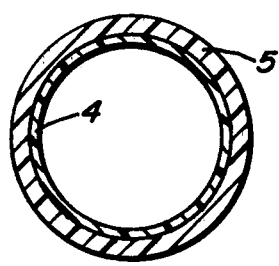
FIG. 6 shows the tube of Embodiment E in which a coating (or film) consisting essentially of cured polyurethane prepolymer is bound (bonded) to the outer surface of the tube comprising immobilized group member.

FIG. 6 shows a tube made of cured polyurethane comprising immobilized biologically active material 4 surrounded by and laminated (i.e., bound or bonded) to a tube consisting essentially of cured polyurethane 5 (i.e., cured polyurethane prepolymer which does not comprise immobilized biologically active material).

Figure 7:
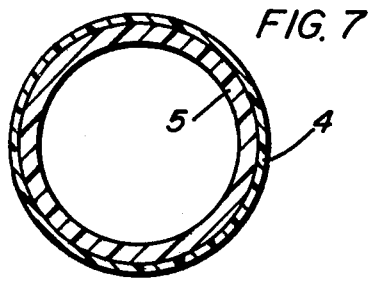
FIG. 7 shows the tube of Embodiment E in which a coating (or film) consisting essentially of cured polyurethane prepolymer is bonded (bound) to the inner surface of the tube comprising immobilized group member.

FIG. 7 shows a tube made of cured polyurethane comprising immobilized biologically active material 4 surrounding and bound (bonded or laminated) to a tube consisting essentially of cured polyurethane 5.

Figure 8:
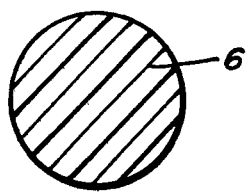
FIG. 8 is a transverse section of the pattern rod of Embodiment F.

FIG. 8 shows inert pattern rod 6.

Figure 9:
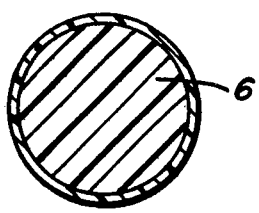
FIG. 9 is a transverse section of the product rod of Embodiment F.

FIG. 9 shows a rod comprising inert pattern rod 6 surrounded by a coating comprising cured polyurethane comprising immobilized biologically active material 4.

Figure 10:
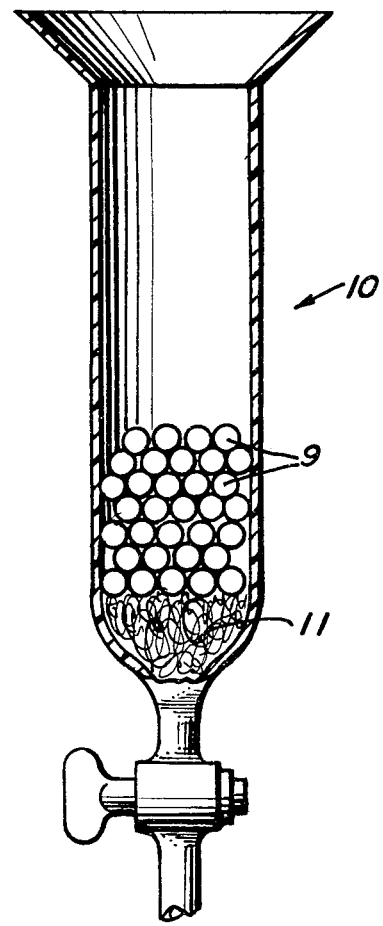
FIG. 10 shows the spheres of Embodiment H packed in a column, the spheres being supported by a packing support (glass wool).

FIG. 10 is a column shown generally at 10 packed with spheres 9 comprising cured polyurethane comprising immobilized biologically active material. Spheres 9 rest on a bed of glass wool 11.

Figure 11:
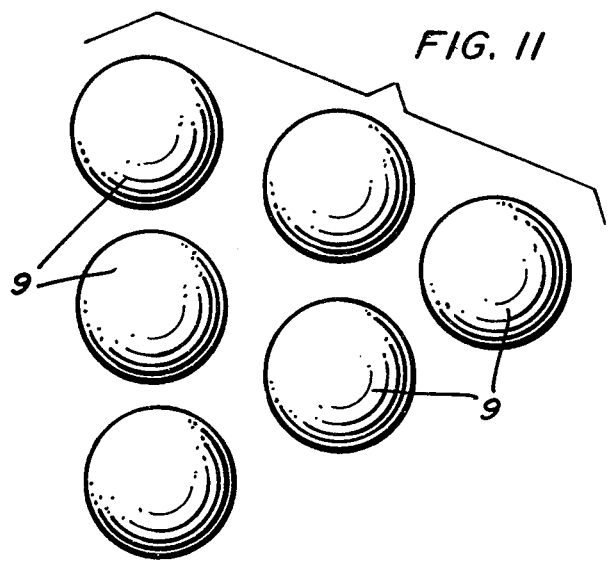
FIG. 11 shows the spheres of Embodiment H.

FIG. 11 shows spheres 9 which are made of cured polyurethane comprising immobilized biologically active material.

Figure 12:
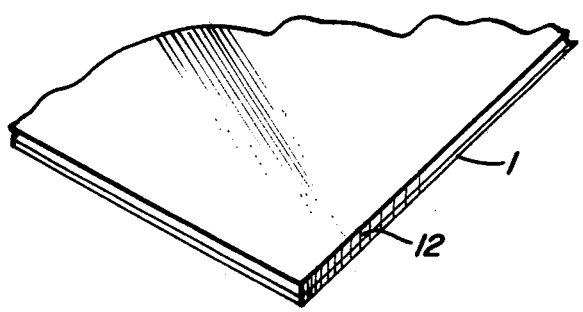
FIG. 12 shows the film of Embodiment C in which said film is bonded (bound) to a second film consisting essentially of cured polyurethane prepolymer.

FIG. 12 shows self supporting film 1 which is made of cured polyurethane comprising immobilized biologically active material bonded (bound or laminated) to film 12 which consists essentially of cured polyurethane.

Figure 13:
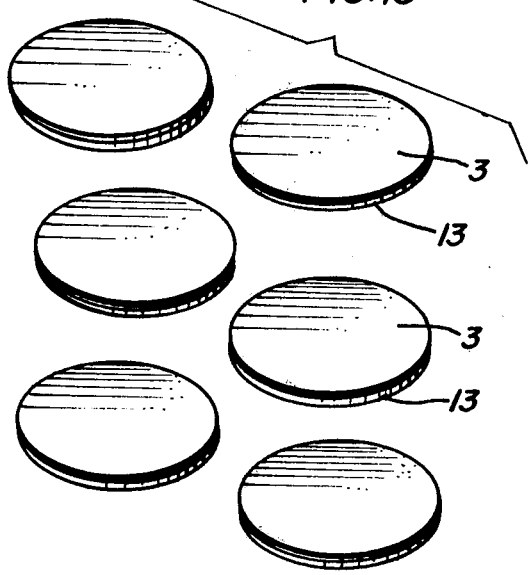
FIG. 13 shows the discs of Embodiment D in which each disc is bonded to a disc consisting essentially of cured polyurethane prepolymer.

FIG. 13 shows self supporting discs 3 which are made of cured polyurethane comprising immobilized biologically active material bonded to discs 13 which consist essentially of cured polyurethane.

FIG. 14 shows inert pattern rod 6 surrounded by a first coating of cured polyurethane which comprises immobilized biologically active material 4, the first coating is surrounded by and bound to a second coating consisting essentially of cured polyurethane 5.

Figure 15:
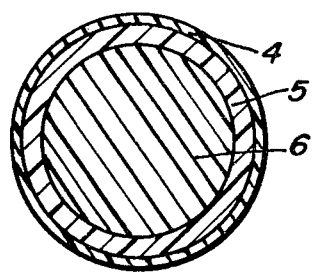
FIG. 15 is a transverse section of the rod of Embodiment F in which the outer surface of the film or coating comprising immobilized group member is coated with a film or coating consisting essentially of cured polyurethane prepolymer.

FIG. 15 shows inert pattern rod 6 surrounded by a first coating consisting essentially of cured polyurethane 5, the first coating is surrounded by and bonded to a second coating of cured polyurethane comprising immobilized biologically active material 4.

Figure 16:
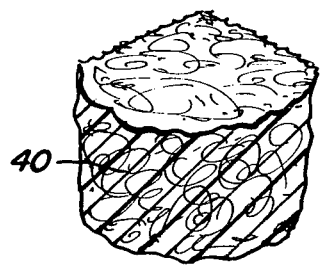
FIG. 16 shows the foam of Embodiment I.

FIG. 16 shows foam 40 which is made of cured polyurethane comprising immobilized biologically active material.

FIG. 17 shows a reactor shown generally at 17.

Reactor 17 comprises:

(a) column 20 having a lower end 22 and an open upper end 21;
(b) cap 23 having an upper portion 24 and an open lower portion, the lower portion of the cap covering and communicating with open upper end 21 of column 20;
(c) inlet line 25 having an inlet port 26 communicating with upper portion 24 of cap 23;
(d) outlet line 30 having an outlet port 31 communicating with lower end 22 of column 20; and
(e) cured self supporting polyurethane foam 29 comprising an immobilized biologically active material selected from the group consisting of: (i) a protein; (ii) a coenzyme having at least one primary or secondary amino group per molecule; (iii) an admixture of said coenzyme and an enzyme which is mediated by said coenzyme; and (iv) an antibiotic having at least one primary or secondary amino group per molecule positioned within the column, said foam being foamed in place in the column.

Outlet line 30 can contain valve 32 (e.g., a stopcock). Reactor 17 can be made of glass or of metal (e.g., stainless steel or the like).

Foam 29 can be formed in place (in situ) in column 20 by:

1. Admixing the biological material (group member) of the above Summary with an excess of the isocyanate-capped liquid polyurethane prepolymer of said Summary to form a resulting mixture (a first mixture or first admixture); forming a second mixture by admixing the first mixture with an amount of water effective for causing the second mixture to foam and for immobilizing the biological material; and placing the second mixture in column 20 while it (the second mixture) is foaming.

2. By foaming a mixture by admixing, in column 20, the group member of said Summary, an excess of the isocyanate-capped liquid polyurethane prepolymer of said Summary, and an amount of water effective for causing the mixture to foam and for immobilizing the group member.

3. By admixing the group member of the aforesaid Summary with water to form an aqueous system and admixing the aqueous system with the isocyanate-capped liquid polyurethane prepolymer of said Summary using a stoichiometric excess of the polyurethane prepolymer and an amount of water effective for causing foaming and for immobilizing the group member. The aqueous system and the polyurethane prepolymer can be admixed in column 20 or in an admixing apparatus and transferred to column 20 while foaming.

Other methods for preparing foam 29 in situ in column 20 will, because of our disclosure, be readily apparent to those skilled in the art.

Techniques for using the product of this invention, i.e., an immobilized biologically active material comprising a foam, a film, a disc, a tube, a sphere, or a rod (any of which can be made by the process of this invention) include, but are not limited to, the following:

1. Passing an aqueous system comprising a reactant through a foam comprising a cured polyurethane comprising the immobilized biologically active material or over a surface comprising a cured polyurethane comprising the immobilized biologically active material.

2. Adding to an aqueous solution comprising a material to be reacted particles of foam comprising cured polyurethane comprising the immobilized biologically active material, or spheres, self supporting discs, particles of tubing, particles of rod, or particles of self supporting film having a surface comprising cured polyurethane comprising the immobilized biologically active material.

Enzymes immobilized by the method of this invention are useful in analytical chemistry and for synthesis reactions. For example, urea can be determined by passing a solution of urea through a column packed with urease immobilized in cured polyurethane foam to quantitatively convert the urea to ammonia which can be determined by titration or by a colorimetric procedure. Spheres, discs, tubes, or rods having surfaces comprising cured polyurethane with urease immobilized thereon can be substituted for the cured polyurethane foam having urease immobilized therein.

The apparatus (reactor) of Embodiment J can be used where the immobilized urease comprises a cured polyurethane foam.

Sucrose can be converted to invert sugar by passing a solution of sucrose over the cured polyurethane in which or on which the urease has been replaced with invertase.

Similarly, these techniques can be used to hydrolize organic esters by replacing the urea solution with an aqueous solution comprising such ester and by replacing the immobilized urease with immobilized lipase.

Where the enzyme is one that requires a coenzyme: (a) both the coenzyme and the enzyme can be immobilized in the cured polyurethane foam comprising the immobilized biologically active material or on the surface of the cured polyurethane article (film, disc, tube, sphere, or rod) comprising the immobilized biologically active material; or (b) either the enzyme or the coenzyme can be immobilized and the other can be present in the aqueous system containing the material (reactant) to be reacted.

For example, ethanol can be dehydrogenated by alcohol dehydrogenase in the presence of the coenzyme $\beta$-nicotineamide adenine dinucleotide ("$\beta$-NAD" which is also called "NAD"). Thus: (a) both the enzyme (alcohol dehydrogenase) and the coenzyme (NAD); or (b) the enzyme; or (c) the coenzyme can be immobilized by the process of this invention and then used to bring about the dehydrogenation of the ethanol.

Where both the enzyme and the coenzyme are immobilized with the cured polyurethane a solution of ethanol is passed over (or through) the cured polyurethane comprising the immobilized enzyme plus the immobilized coenzyme. Where only the enzyme is immobilized (bound) a solution comprising alcohol and the coenzyme is passed over (or through) the cured polyurethane comprising the immobilized enzyme. Where only the coenzyme is bound a solution comprising alcohol and the enzyme is passed over (or through) cured polyurethane comprising the bound coenzyme.

Immobilized (bound) antigens prepared by the method of this invention are useful for removing antibodies from biological samples. For example, immobilized (bound) human immunoglobulin G (IgF) is useful for removing rheumatoid arthritis factor (an antibody) from human blood.

Immobilized (bound) antibodies prepared by the method of this invention are useful for removing antigens from biological samples. For example, the antibody of hepatitis can be immobilized (bound) according to the process of this invention, and the resulting bound (immobilized) antibody can be used to remove the hepatitis antigen from blood (e.g., blood in blood banks).

The bound (immobilized) biological material (biologically active material) of this invention has a long service life.

For example:

1. Where the bound (immobilized) biological material (the group member of the above Summary) is an enzyme, a coenzyme having at least one primary or secondary amino group per molecule or an admixture of such coenzyme and an enzyme mediated by the coenzyme it (the immobilized biological material) does not lose its activity even where used for hundreds of hours.

2. Where the immobilized (bound) biological material is an antigen (useful for removing an antibody from an aqueous system) it will become spent ("saturated") when it has taken up an equivalent amount of antibody. It then becomes necessary to regenerate the bound antigen (i.e., to free it of antibody). This can be done by washing with an aqueous regenerating solution (e.g., by passing such regenerating solution through a column packed with the immobilized antigen and then washing the regenerating solution from the regenerated column). An aqueous glycine hydrochloride solution (for example, 0.15–3 molar, preferably about 0.5 molar) is an excellent regenerating solution. Such glycine hydrochloride solution has a pH of about 2.5.

3. Where the bound (immobilized) biological material is an antibody (useful for removing an antigen from an aqueous system) it will become spent (saturated) when it has taken up an equivalent amount of antibody. It then becomes necessary to regenerate the bound protein (i.e., to free it of antigen). This can be done by washing with an aqueous regenerating solution such as the above described glycine hydrochloride solution (e.g., by passing the regenerating solution through a packed column packed with the immobilized antibody and washing the regenerated column as above).

4. Where the immobilized (bound) biological material is an antibiotic it will become spent or partially spent on extended use—i.e., it loses its antibiotic properties or such properties become substantially reduced. Such spent or partially spent immobilized antibiotic can be regenerated by washing with a sterile solvent such as sterile water or sterile saline solution, or the like. For example, sterile water can be passed through a column packed with the antibiotic or rods, tubes, or films can be flushed with sterile water.

The instant invention will be better understood by referring to the following specific but nonlimiting examples and procedures. It is understood that said invention is not limited by these examples and procedures which are offered merely as illustrations; it is also understood that modifications can be made without departing from the spirit and scope of the invention.

The examples were actually run.

The procedures, while not actually run, will illustrate certain embodiments of our invention.

EXAMPLE 1

(Preparation of Prepolymer)

An isocyanate-capped liquid polyurethane prepolymer was prepared by reacting 2 milliequivalents (meq), 1 g, of a polyethylene glycol having an average molecular weight of 1000 with 2.63 meq, 0.229 g, of toluene diisocyanate. The resulting prepolymer was designated "Prepolymer #1".

A replication of the above procedure was repeated wherein said procedure was modified by using 20 meq of the polyethylene glycol and 26.3 meq of the toluene diisocyanate to form a second lot of Prepolymer #1. Additional lots were prepared as needed.

EXAMPLE 2

(Preparation of Prepolymer)

Two moles of a polyethylene glycol having an average molecular weight of 1,000 (PEG 1,000) and one mole of trimethylolpropane (TMP) were admixed and dried at 100°–110° C. under a pressure of 5–15 Torr to remove water. The resulting dried mixture, which contained a total of 7 moles (119 g) of reactive terminal hydroxyl (—OH) groups, was slowly added (taking about an hour) to a vessel containing 6.65 moles of toluene diisocyanate (TDI) while stirring the TDI and the resulting mixture. The TDI and the resulting mixture in the vessel were maintained at 60° C. The resulting mixture was stirred for 3 hours, while maintaining it at about 60° C., after all of the PEG 1,000-TMP mixture had been added to the reaction vessel. Then an additional 1.05 mole of toluene diisocyanate was added and stirring was continued for an additional hour while maintaining the stirred mixture at about 60° C. Thus, a 10 molar percent excess of the TDI was added to the PEG 1,000-TMP mixture. This assured that all hydroxyl groups of the polyols (the PEG 1,000 plus the TMP) were capped with isocyanate and that some chain extension occurred because of crosslinking of the polyols with the excess TDI.

The resulting liquid isocyanate-capped polyurethane prepolymer which resulted was designated "Prepolymer #2". Additional lots of Prepolymer #2 were prepared as needed.

EXAMPLE 3

(Preparation of Prepolymer)

An isocyanate-capped liquid polyurethane prepolymer was prepared by reacting 31 g of glycerol (glycerine) with an amount of ethylene oxide to form 500 g of an intermediate compound (a hydroxyl-capped polyether) having an equivalent weight of about 500 (i.e., containing about 17 g of —OH group per 500 g of intermediate compound). This intermediate compound was reacted with commercial toluene diisocyanate using 1.05 mole of the toluenediisocyanate per 500 g of the intermediate compound. The resulting isocyanate-capped liquid polyurethane prepolymer was designated "Prepolymer #3". Additional lots of Prepolymer #3 were prepared as needed.

EXAMPLE 4

A solution of 10 mg Adenosine-5-Triphosphate (ATP) in 1.0 gm water was added to 1.0 gm of Prepolymer #2. The resultant solution was allowed to react at 28° while stirring for about five minutes. After an additional five minutes without stirring, the binding reaction and foam formation were complete. The foam was washed thoroughly with water. The total wash water was collected and analyzed for ATP by ultraviolet spectrophotometry. It was found that 9.5 mg of the ATP initially charged was washed out of the foam by the wash water. In other words, 5% of the ATP originally charged was bound to the polyurethane foam.

EXAMPLE 5

A solution was made by mixing 20 mg of ATP with 2 ml of water for ten minutes until dissolved. A 1.0 ml portion of this solution was mixed with 1.0 gram of Prepolymer #1. The resulting system began to foam and within ten minutes foam formation was complete. The resulting foam was thoroughly washed with water. The wash water was collected and analyzed for ATP by ultraviolet spectrophotometry. It was found that 4% of the ATP initially charged was bound to the polyurethane foam.

EXAMPLE 6

A solution was prepared of 1.0 gram Prepolymer #3 and 300 mg β-Nicotinamide-Adenine Dinucleatide (β-NAD). After reacting for 15 minutes in a dry atmosphere, distilled water was added and stirred for one minute. The resulting product began to foam within 35 seconds and foam formation was complete within 10 minutes. The resulting foam was ground in a mortar with pestle until a fine particle material was obtained. The particles were then washed thoroughly in 100 ml of distilled water. Ultraviolet absorption (260 m$\mu$) of the wash water showed the presence of 218 mg NAD and, therefore, 82 mg NAD was bound to the foam. Additional washings of the foam with small amounts of water showed no additional NAD was washed out.

EXAMPLE 7

An admixture was prepared of 1.0 gram of Prepolymer #2 with 10 mg of Alcohol Dehydrogenase and 10 mg of β-Nicotinamide Adenine Dinucleatide (β-NAD).

After reacting for 15 minutes in a dry atmosphere, 1.0 gm distilled water was added to the product and stirred for one minute. The product began to foam and within 10 minutes foam formation was complete. The resulting foam was thoroughly washed with water.

The foamed system was then assayed against equal portions of free enzyme and coenzyme by measuring the decrease in concentration of an ethanol substrate by assaying aliquot samples from both reaction mixtures using the dichromate titration method of Harger (J. Biol. Chem. 183, 197 [1950]).

It was found that the foamed enzyme-coenzyme system was enzymatically active, and the rate was 5% of that of the free activity of the free system.

EXAMPLE 8

A mixture was prepared by mixing 1.0 gram of prepolymer #2 and 10 mg of Adenosine-5-Triphosphate (ATP). The resulting mixture was stirred while reacting at 25° for 15 minutes. Water (1 gm) was added to the product while stirring. The resulting water-containing system began to foam and within 10 minutes foam formation was complete. The foam was then washed thoroughly with water. The wash water was collected and analyzed for ATP by ultraviolet spectrophotometry. It was found that 7 mg of the ATP initially charged was washed out of the foam by the wash water. In other words, 30% of the ATP originally charged was bound to the polyurethane foam.

EXAMPLE 9

A mixture was prepared by mixing 10 mg of ATP with 1.0 gram of Prepolymer #1 for 15 minutes in a dry atmosphere at ca. 25° C. Then a 1.0 gram portion of water was added to the mixture at ca. 25° C. while stirring. The resulting water-containing system began to foam and foam formation was complete within 10 minutes. The foam was then washed thoroughly with water. The wash water was collected and analyzed for ATP by ultraviolet spectrophotometry. It was found that 32% of the ATP initially charged was bound to the polyurethane foam.

EXAMPLE 10

A mixture was prepared by mixing 1.0 gram of Prepolymer #1 with 10 mg of Adenosine-5-Diphosphate (ADP). The resulting mixture was stirred for 15 minutes in a dry atmosphere (to prevent foam formation due to atmospheric moisture). Then a 1 ml portion of water was added while stirring. The resulting water-containing system began to foam, and within 10 minutes foam formation was complete. The resulting foam was cut up and thoroughly washed with 100 ml of d $H_2O$. The wash water was collected and analyzed for ADP by ultraviolet spectrophotometry. It was found that 15% of ADP initially charged was bound to the polyurethane foam.

EXAMPLE 11

Example 10 was repeated using 10 mg of Nicotinamide-Adenine Dinucleotide Phosphate (NADP). The foam had bound 20% of the initially charged coenzyme.

EXAMPLE 12

Example 10 was repeated wherein said procedure was modified by using 100 mg of Thiamine Pyrophosphate and 0.9 grams of Prepolymer #1; and reacting at room moisture for 15 minutes. The foam had bound 13% of the initially charged coenzyme.

EXAMPLE 13

Example 10 was repeated except Flavin Adenine Dinucleotide (FAD) was used as the coenzyme. Of the total coenzyme in the reactant step, 38% was bound after washing.

EXAMPLE 14

Example 10 was repeated except Flavin Mononucleotide (FMN) was used. A 33% binding level was achieved.

EXAMPLE 15

A 10 mg sample of $\beta$-Nicotinamide-adenine dinucleotide ($\beta$-NAD) was mixed with one gram of Prepolymer #2 for 15 minutes in a dry atmosphere and then 1 ml of water was added and mixed thoroughly. Foam formation was complete within 10 minutes. The foam was cut up and washed thoroughly. The foam was assayed for activity using an ethanol solution containing 10 mg of free alcohol dehydrogenase.

The foam was found to be active in converting the ethanol to acetaldehyde.

EXAMPLE 16

A coenzyme bound to a non foamed cured polyurethane was prepared in the following manner:

An admixture of two grams of Prepolymer #2 with 27 mg of the coenzyme Nicotinamide adenine dinucleotide was prepared and reacted for 15 minutes. This material was then mixed with two grams of acetone. The resulting solution was poured into a petri dish and allowed to cure. The resulting non foamed polyurethane bound coenzyme was washed with water. The wash water was collected and analyzed for Nicotinamide adenine dinucleotide by ultraviolet spectrophotometry. It was found that 28% of the Nicotinamide adenine dinucleotide initially charged was bound to the non foamed polyurethane.

EXAMPLE 17

A coenzyme was bound to a non foamed polyurethane and tested according to the general procedure of Example 16. However, 16 mg of the coenzyme Flavin Mononucleotide was used instead of Nicotinamide adenine dinucleotide.

It was found that 21% of the Flavin Mononucleotide initially charged was bound to the non foamed polyurethane.

EXAMPLE 18

A coenzyme bound to a non foamed polyurethane was prepared in the following manner.

An admixture was prepared by mixing one gram of prepolymer as described in Example 16 with one gram of acetone. This mixture was then stir-added to an admixture consisting of one gram of water and 20 mg of Flavin Mononucleotide. The two liquids were mixed together until a clear liquid resulted (1-2 min.). The liquid was then poured in a thin layer over a glass plate and left to cure for 30 minutes. The non foamed polyurethane was then removed from the plate, cut up, washed, and the wash water assayed for Flavin Mononucleotide by ultraviolet spectrophometry.

It was found that 95% of the Flavin Mononucleotide was bound to the non-foamed polyurethane.

EXAMPLE 19

A 40mg sample of peroxidase was mixed with one gram of Prepolymer #2. This sample was then added to 3 ml. of acetone and mixed. The resulting solution was poured into a petri dish, and the acetone was allowed to evaporate at room conditions overnight while the prepolymer/enzyme sample cured via room moisture. The material dried in a thin film. The sample was washed and assayed for peroxidase activity using a 3% peroxide solution containing p-phenylanaline diamine. The sample was repeatedly active towards peroxide.

EXAMPLE 20

A 1:4 acetone/Prepolymer #2 solution (weight basis) was prepared by dissolving 4 parts of Prepolymer #2 in acetone. This solution was poured into a petri dish and allowed to cure for 16 hours by room moisture while the acetone evaporated. A clear translucent sheet of polyurethane film was removed from the plate. This film was then used to make polyurethane discs by punching out circles on the film.

EXAMPLE 21

Bound antibiotic discs were made in a similar manner as Example 20. However, the prepolymer contained 10 mg of ampicillin per 2 gm of prepolymer before being mixed with an equal weight of acetone.

The discs were thoroughly washed and tested for activity. The bound ampicillin discs and control were placed on E. coli-inoculated agar plates. The E. coli growth spread over the agar, however, not over or under the bound ampicillin disc surface.

There was an absence of a zone of inhibition formed in the agar due to the ampicillin being bound to the disc. There was no growth on the surface of the disc due to surface bound ampicillin. By contrast the control disc (no ampicillin) did not inhibit growth of E. coli on the disc surface.

EXAMPLE 22

Bound urease polyurethane film and discs were made by the following procedure: A 20 gram sample of Prepolymer #2 was mixed with and dissolved in 20 grams of acetone to form a solution designated "Solution A".

A 100 mg sample of urease was mixed with one ml of water until dissolved to form a solution designated "Solution B". Solution B was added to Solution A at a slow rate while stirring gently until all of Solution B was added. The resulting mixture was then poured on a glass plate, spread to form a film, and allowed to cure for one hour. The resulting cured film was removed and discs were punched from this film.

The discs were assayed for urease activity and found to be active in a series of runs where using an aqueous solution of urea as reactant. The urea was hydrolyzed.

EXAMPLE 23

A 10 gram sample of polyurethane prepolymer (Prepolymer #2) was admixed with one gram of Pluronic L-64 (a nonionic surfactant) to reduce viscosity. This mixture was then coated on the inside of a 6" length of glass tubing—interior diameter 4 mm—by use of a vacuum pulling the mixture into the tube. The coating was cured by pulling moist air (relative humidity about 50%) through the tube by vacuum suction. The result was a glass tube with a cured nonfoamed polyurethane coating covering its interior surface.

EXAMPLE 24

The procedure of Example 23 was repeated except that the Pluronic L-64 was omitted and a 10 gram portion of water was mixed with a 10 gram portion of the prepolymer. While foaming was taking place, the material was vacuum pulled through a section of glass tubing. The result was a glass tube that was completely coated on the inside with a thin layer of cured polyurethane, with an open channel through the tubing.

EXAMPLE 25

The general procedure of Example 23 was repeated; however the Pluronic L-64 was used at a rate of 3 parts to 10 parts of prepolymer. Also, the tube was left to cure slowly in a drying oven for 48 hours. The result was a glass tube which was completely coated on its inner surface with cured polyurethane, with an open channel through the tubing.

EXAMPLE 26

A sample of prepolymer, as described in Example 23 was vacuum-pulled through a glass tubing as described in Example 23 leaving a thin layer of prepolymer coating on the inner surface of the tubing. A stream of moist air was pulled over the layer by vacuum for 18 hours. The result was that a thin translucent film of polyurethane was formed on the inner surface of the tubing.

EXAMPLE 27

The general procedure of Example 26 was repeated. However, in this instance, after curing the prepolymer, a second coating of prepolymer was applied to the first (i.e., the cured) coat of prepolymer. This procedure was repeated until a total of 6 coatings had been applied and cured. On curing, each coat became bonded to (and was a part of) the coat to which it had been applied. The glass tube was broken and removed from the resulting tube consisting essentially of cured polyurethane which was a translucent cured polyurethane tube which could pass fluids without leakage.

EXAMPLE 28

The general procedure of Example 26 was repeated. However, a rubber tube having an inside diameter of ⅛ inch was used as a pattern tube. The product was a rubber tube lined with a coat of cured polyurethane.

EXAMPLE 29

The general procedure of Example 27 was repeated. However, in this instance, the final (sixth) coat of polyurethane prepolymer applied to the system contained 86 mg of jack bean urease. The resulting tube (the tube consisting essentially of cured polyurethane (cured polyurethane prepolymer) which surrounded and was bonded to a tube comprising cured polyurethane (cured polyurethane prepolymer) comprising immobilized jack bean urease was thoroughly washed with water. A buffered (pH 7) urea solution, 80 mg %, was passed through the tube. The effluent was titrated for presence of ammonia. It was found that 33μ moles of $NH_3$ were present per ml of effluent. This shows that urease was bound (i.e., immobilized) in an active form.

EXAMPLE 30

Glucose oxidase was bound to polyurethane tubing by the general procedure of Example 29, except that 8 mg of glucose oxidase was used in place of the urease of Example 29. The tube was assayed for activity using a glucose solution, 90 mg %, and found to retain, through repeated testing, about 95% of its initial activity where the glucose solution used in the assay contained peroxidase.

EXAMPLE 31

A 26 cm length of glucose oxidase/peroxidase bound cured polyurethane tube made (with glucose oxidase/peroxidase as biological material) by the general procedure of Example 29 was tested in an Autoanalyzer system for the determination of glucose. Said tube was a tube of the type represented by FIG. 5, i.e., it comprised an outer coat of cured polyurethane having an inner coat laminated thereto, the inner coat comprising non-foamed cured polyurethane comprising immobilized glucose oxidase/peroxidase. Said tube was found to be operable for the quantitative determination of glucose in the Autoanalyzer system.

EXAMPLE 32

An 8.5 length of peroxidase bound cured polyurethane tubing (made by the general procedure of Example 30, but with peroxidase as the biological material to be bound) was assayed in an Autoanalyzer system, using free (unbound) glucose oxidase. The tubing was found to be accurate for the quantitative determination of glucose in the Autoanalyzer system.

EXAMPLE 33

A 120 cm length of glucose oxidase bound polyurethane tubing was made by the general procedure of Example 30 except that the outercoat (i.e., the coat corresponding to "5" in FIG. 6 which consisted essentially of cured polyurethane (cured polyurethane prepolymer)) was made from a mixture of prepolymer and acetone (1 part prepolymer and 3 parts acetone). The last (fifth) coat consisting essentially of isocyanate-capped liquid polyurethane prepolymer (which was applied to and cured on the fourth coat of cured polyurethane prepolymer) was admixed with calcotone blue (a dye) before being applied. Said fifth coat was cured and then coated with an isocyanate-capped liquid polyurethane prepolymer comprising glucose oxidase which was cured to form an inner coat (corresponding to "4" of FIG. 6) comprising cured polyurethane (cured polyurethane prepolymer) comprising immobilized glucose oxidase. Said tube was tested and found to be operable for the determination of glucose (where using free (i.e., nonbound (i.e., not immobilized)) peroxidase in the aqueous solution comprising glucose) in an Autoanalyzer system.

EXAMPLE 34

A 60 cm length of urease bound polyurethane tube was made by the general procedure of Example 29. In this instance the tube was prepared by coating the interior surface of a 60 cm length of glass tubing with 20 coats of a prepolymer/acetone solution (one part prepolymer+three parts acetone). The solution was pulled through the tubing to thoroughly coat. After applying each coat air was continually passed through the tube to permit moisture present in the air to cure the coat. After 20 coats were applied and cured, a 2.7 mg portion of jack bean urease was applied to the tubing in the final coat of isocyanate-capped liquid polyurethane prepolymer which was cured as above to form a tube of the type represented by FIG. 6.

The resulting tube was washed and assayed for activity in an Autoanalyzer system for the conversion of urea to ammonia and found to be operable for the determination of urea in the Autoanalyzer system.

EXAMPLE 35

A stainless steel rod (36" long; 1/16" diameter) was dip-coated six times in 1:1 acetone/prepolymer solution (Prepolymer #2). Each coat was allowed to cure in moist air before the next coat was applied. The resulting article was a steel rod coated with a coat consisting essentially of cured polyurethane. The steel rod was removed from the coating by soaking in water. The result was a cured polyurethane tube (36" long with inside diameter of 1/16").

EXAMPLE 36

The same general procedure was followed as in Example 35, except that a glass rod (12 cm long having a 5 mm diameter) was used instead of a metal rod. The resulting article was a glass rod coated with a coat consisting essentially of cured polyurethane. The glass rod was separated from the coating to form a tube consisting essentially of cured polyurethane.

EXAMPLE 37

The same general procedure was followed as in Example 36 except that a quartz rod (30 cm long, 1.5 mm diameter) was used instead of glass. The end product was a 30 cm long cured polyurethane tube 1.5 mm inside diameter.

EXAMPLE 38

A 36" glucose oxidase bound cured polyurethane tube was made by the general procedure of Example 35. However, before the 5 prepolymer/acetone coats are applied and cured, a coat of prepolymer/enzyme material was applied in a thin layer, covering the rod surface, and cured by exposure to room moisture (i.e., moist air). The final product (after removing the steel rod) was a tube of the type shown in FIG. 6.

The tube was tested for activity in an Autoanalyzer system using a glucose solution containing free peroxidase and found to be operable for determining glucose.

EXAMPLE 39

A 36" peroxidase bound cured polyurethane tube was made by the general procedure of Example 38. However, 7 mg of peroxidase (rather than glucose oxidase) was included in the first prepolymer/enzyme coat.

The product tube was tested for activity in an Autoanalyzer system using a glucose solution containing free glucose oxidase and found to be active.

EXAMPLE 40

A urease bound cured polyurethane tube was made in the general procedure of Example 38, except the initial prepolymer/enzyme coat contained urease at a 5% dry weight basis.

A solution of 200 mg % urea was passed through the tube at a rate of 1.75 ml/min.

The tube was found operable as a source of urease for the determination of urea.

EXAMPLE 41

A bound urease cured polyurethane tube was made by the general procedure of Example 38, but modified by using urease rather than glucose oxidase. However, after the polyurethane prepolymer/enzyme coat was applied and cured, 14 coats (rather than 5) of prepolymer/acetone solution were applied and cured to make a thicker walled tube than in Example 38.

The product tube was found to be active towards a urea solution (i.e., it hydrolyzed urea present in an aqueous urea solution which was passed through it (the product tube)).

EXAMPLE 42

A bound urease cured polyurethane tube was made by the general procedure of Example 41. However, the enzyme/prepolymer coat contained 25% urease on a dry basis.

The product tube was tested in a continuous run whch lasted for 480 hours by passing 34,000 ml of a 200 mg % urea solution through said tube. No loss of activity was detected.

EXAMPLE 43

Polyurethane prepolymer (Prepolymer #2) was dropped from a size 20 syringe needle into a 4 foot high column filled with a solution of 0.748 mg % ethylenediamine (EDA) in water. The drop was allowed to fall while curing. Upon examination, the product was spherically shaped.

EXAMPLE 44

Two replications were run using the general method of Example 43. However, said general method was modified by using an aqueous solution containing: (a) 1.496 mg % EDA in one replication; and (b) 2.992 mg % EDA in the other. The results of these replications were indistinguishable from those obtained in Example 43.

EXAMPLE 45

Polyurethane prepolymer (Prepolymer #2) was mixed in a 50/50 weight ratio with acetone. This solution was then dropped dropwise into a 4 foot long column reactor filled with water. The solution clouded up near and on the top surface of the water. From this cloud, small particles formed and fell slowly to the bottom of the reactor. The particles were examined and found to be spherical in shape.

EXAMPLE 46

A 10 mg sample of urease (Miles) was mixed with 1 gram of Prepolymer #2. After 15 minutes 1 gram of acetone was added thereto and the resulting mixture was stirred until a clear liquid resulted (ca. 1-2 minutes). The resulting solution was dropped one drop at a time into a 4 foot column filled with 0.748 mg % EDA in water. The top portion of the column became cloudy and from this cloud streamers of curing polyurethane prepolymer sank toward the bottom of the column. As these streamers fell, they divided (broke up) into spherical particles. After the particles settled out, they were collected by vacuum filtration and washed with water. The spherical particles were then assayed, after washing, for urease activity; a 20% activity retention level was observed. The particles were then dried and screened. The majority of the particles fell within a 0.5-1 mm range.

PROCEDURE 1

An enzyme and an antibiotic can be bound (immobilized) in the same article (cured polyurethane prepolymer comprising a foam, a film, a disc, a tube, a rod, or a sphere); for example:

A first admixture can be prepared by admixing 100 g of an isocyanate-capped liquid polyurethane prepolymer (e.g., Prepolymer #1, Prepolymer #2, or Prepolymer #3), 5 g of invertase and 5 g of an antibiotic having at least 1 primary or secondary amino group per molecule (e.g., ampicillin, bacteracin, colistin, or neomycin). Said first admixture can be cured to produce a foam comprising the cured polyurethane prepolymer comprising immobilized invertase and immobilized antibiotic—immobilized ampicillin, immobilized bacitracin, immobilized colistin, or immobilized neomycin—by admixing it (the aforesaid first admixture) with water to form a second admixture using an amount of water (e.g., 200 g) effective for foaming and curing the prepolymer component of the second admixture and for forming a cured polyurethane prepolymer foam comprising immobilized invertase plus the immobilized antibiotic.

The thus produced foam, or a portion thereof, can be packed into a column, or: (a) the first admixture can be foamed in place in the apparatus of Embodiment J (FIG. 17); or (b) the second admixture, while still foaming, can be transferred to said apparatus (the apparatus of Embodiment J).

An aqueous sucrose solution (e.g., 100-10,000 mg % sucrose) which has been contaminated with bacteria (e.g., E. coli) can be passed into the column which was packed with the above described foam in an attempt to "contaminate" or "innoculate" the apparatus, and allowed to stand therein for 8-10 hours at about 25°. Then sterile aqueous sucrose solution (e.g., 100-10,000 mg % sucrose) can be passed through the apparatus to form invert sugar which will be substantially free of (a) bacteria induced decomposition products; and (b) said bacteria (E. coli).

Where using a similar procedure with a similar foam comprising immobilized invertase but not immobilized antibiotic, the invert sugar product will be contaminated with decomposition products (e.g., cellular debris, other sugars, carbon dioxide, alcohols, etc.) and the bacteria (i.e., E. coli).

PROCEDURE 2

An ordinary sucrose solution which is slightly contaminated with bacteria such as E. coli or bacillus subtilis can be converted to invert sugar which is substantially free of bacteria by passing such sucrose solution through a column packed with cured polyurethane foam comprising immobilized invertase and one or more of the immobilized antibiotics of Procedure 1.

A cured polyurethane prepolymer film comprising an immobilized antibiotic—the antibiotic being one which (before being immobilized) had at least one primary or secondary amino group per molecule)—can be used as a dressing for wounds and abrasions on animals (including mammals) to prevent or inhibit the development of infection in such wounds or abrasions.

As used herein, the terms "immobilized" and "bound" as applied to a biological material, i.e., a group member as recited in the above Summary, means that the bound or immobilized group member is no longer mobile where placed in contact with a liquid in which it (the biological material) is soluble in the free state and that it (the immobilized biological material) is insoluble in said liquid. For example, a group member dissolved in an excess of an isocyanate-capped liquid polyurethane prepolymer exists in the liquid state and is not immobilized; however, it becomes immobilized when the liquid polyurethane prepolymer is cured—e.g., by reaction with water or an amine. Likewise, a group member dissolved in water is mobile and not immobilized. A pure water soluble enzyme, antibiotic, coenzyme, antigen, or antibody—although in the solid state—is not immobilized because, if 1 part of such solid group member is added to about 5–100 or 10–50 parts of water such solid enzyme, antibiotic, coenzyme, antibody, or antigen will dissolve and become mobile. A "bound" (immobilized) group member (member of the group recited in said Summary) will not dissolve and become mobile if treated with such ratios or quantities of water or with much larger quantities of water. In the process of this invention the isocyanate-capped liquid polyurethane prepolymer is the immobilizing agent (binding agent) because it brings about the immobilization (binding) of the biological material.

The term "mediated" as applied to an enzyme-coenzyme-reactant(s) system means that the coenzyme effects, by acting as an intermediate between the enzyme and a reactant (or reactants), catalytic activity in the system with the enzyme plus the coenzyme serving as the catalyst for a reaction involving the reactant(s).

The term "cure" as applied to an isocyanate-capped liquid polyurethane prepolymer means that such prepolymer reacts with a material called a "curing agent" to further polymerize the prepolymer to produce a large water insoluble molecule which is a solid at 25°. Water and amines (primary or secondary amines) are preferred curing agents.

Where immobilizing a biological material by the process of this invention the reaction and manipulative steps are conducted at temperatures below the denaturation temperature of the biological material or below 120°, whichever is lower.

As used herein: (a) the symbol (#) means number; (b) the symbol (") means inch or inches (thus 3" means 3 inches and 1/16" means 1/16 inch); (c) the symbol (%) means percent; (d) the term (mg %) means milligram percent (i.e., 1 mg % = 10 ppm); (e) (g or gm) means gram(s); (f) (mg) means milligram(s); (g) ($\mu$) means micron(s); (h) (cm) means centimeter(s); (i) (mm) means millimeter(s); and (j) (m$\mu$) means millimicron(s)

All parts and ratios are parts or ratios by weight unless otherwise defined where used, and percent and milligram percent are by weight.

All temperatures are in degrees centigrade unless otherwise defined where used. Thus 25° means 25 degrees centigrade, and 120° means 120 degrees centigrade.

As used herein the term "polyisocyanates" includes diisocyanates.

The isocyanate-capped liquid polyurethane prepolymers used in this invention contain at least two isocyanate groups (reactive isocyanate groups) per molecule of prepolymer. Isocyanate-capped polyurethane prepolymers are "liquid" polyurethane prepolymers if they are free flowing liquids at 40°–70°.

A foam which is not soluble in water is considered to be a solid.

Unless another solvent is specified where describing a solution, the solution is an aqueous solution (i.e., a solution comprising water).

The term "free" where applied to an enzyme or coenzyme means that the enzyme or coenzyme is not bound (i.e., not immobilized).

The films of polyurethane prepolymer, or such prepolymer plus biological material which are cured to form films of cured prepolymer or films of cured prepolymer comprising immobilized biological material are generally less than 5 mm thick—generally about 0.5–1 mm thick.

As used herein the term "isocyanate-capped liquid polyurethane prepolymer" means any isocyanate-capped polyurethane prepolymer which is: (a) a free flowing liquid at about 40°–70° C.; or (b) can be dissolved in an inert solvent to form a solution (containing about 1–99% by weight (or about 10–90% by weight) of the prepolymer) which is a free flowing liquid at about 40°–70° C.

Ppm (i.e., ppm) means parts per million by weight.

We claim:

1. A process for immobilizing a biological material selected from the group consisting of: (a) a protein; (b) a coenzyme having at least one primary or secondary amino group per molecule; (c) an admixture of said coenzyme and an enzyme; and (d) an antibiotic having at least one primary or secondary amino group per molecule, the process comprising:
   A. contacting the group member and an excess of an isocyanate-capped liquid polyurethane prepolymer in the absence of water to form a resulting mixture where said prepolymer is the reaction product of a polyether polyol with sufficient polyisocyanate to provide at least two free NCO groups per molecule of the prepolymer;
   B. shaping the resulting mixture; and
   C. curing the shaped resulting mixture by contacting it with a curing agent to form a cured shaped article comprising the immobilized biological material.

2. The product prepared by the process of claim 1.

3. The process of claim 1 in which the isocyanate-capped liquid polyurethane prepolymer is prepared by reacting toluene diisocyanate and a polyethylene glycol.

4. The process of claim 1 in which the isocyanate-capped liquid polyurethane prepolymer is prepared by reacting toluene diisocyanate and a polyethylene glycol having a molecular weight of about 800–1,200.

5. The process of claim 1 in which the isocyanate-capped liquid polyurethane prepolymer is prepared by reacting toluene diisocyanate and a member selected from the group consisting of a polyoxybutylene polyol polymer, a polyoxyethylene polyol polymer, a polyoxypropylene polyol polymer, and propylene oxide/ethylene oxide copolymers.

6. The process of claim 1 in which the isocyanate-capped liquid polyurethane prepolymer is prepared by reacting toluene diisocyanate with an admixture of a polyethylene glycol having a molecular weight of about 800–1,200 and trimethylolpropane, the trimethylolpropane and the polyethylene glycol being provided in a mole ratio of about 1:1–4 and the toluene diisocyanate being provided at a rate of about 1–1.25 mole per equivalent of —OH provided by the polyethylene glycol plus the trimethylolpropane.

7. The process of claim 1 in which the cured product is washed to remove unbound nonimmobilized group member and to hydrolyze any unreacted isocyanate groups.

8. The process of claim 1 in which the curing agent is in vapor form.

9. The process of claim 8 in which the curing agent in vapor form is contained in an inert gas.

10. The process of claim 9 in which the inert gas is air, nitrogen, oxygen, carbon dioxide, hydrogen, argon, helium, xenon, or a mixture of at least 2 of said inert gases.

11. The process of claim 1 in which the curing agent is water.

12. The process of claim 1 in which the curing agent is an amine having zero to about 10 carbon atoms per molecule and at least one primary or secondary amino group per molecule.

13. The process of claim 12 in which the curing agent is
ammonia,
hydroxylamine,
hydrazine,
diethylenetriamine
propylamine,
butylamine,
ethylenediamine, or
aniline.

14. The process of claim 1 in which the group member is the protein.

15. The process of claim 14 in which the protein is an enzyme, an antibody, or an antigen.

16. The process of claim 15 in which the enzyme is
urease,
trypsin,
lactase,
glucose oxidase,
chymotrypsin,
ribonuclease,
peroxidase,
pepsin,
rennin,
invertase,
papain,
asparaginase,
pectinase,
pectin esterase,
penicillin amidase,
glucose isomerase,
lysozyme,
amino acid acylase,
pronase,
alcohol dehydrogenase,
α-amylase,
β-amylase,
subtilisin,
amino acid oxidase,
catalase,
tannase,
phenol oxidase,
glucoamylase,
pullulanase,
cellulase,
ficin,
bromelain,
pancreatin,
isoamylase,
lipase,
malic dehydrogenase,
hexokinase,
lactate dehydrogenase,
adenosine deaminase,
uricase,
galactose oxidase,
diaphorase,
cholinesterase,
aldolase,
pyruvate carboxylase,
phospharylase,
cephalosporin amidase,
isocitric dehydrogenase,
α-glycerolphosphate dehydrogenase,
glyceraldehyde-3-phosphate dehydrogenase,
malic enzyme,
glucose-6-phosphate dehydrogenase,
5-dehydroshikimic reductase,
glutathione reductase,
glycolic acid oxidase,
yeast cytochrome c reductase,
luciferase,
nitrite reductase,
glutamyl transferase,
glutathione synthetase,
glycocyamine phosphokinase,
hippuric acid synthetase,
aldehyde oxidase,
succinic dehydrogenase,
nitrate reductase,
xanthine oxidase,
lipoyl dehydrogenase,
flavin peroxidase,
glycine oxidase,
carboxylase,
α-keto acid dehydrogenase, or
transketolase.

17. The process of claim 15 in which the antibody is human immunoglobulin G or hepatitis antibody.

18. The process of claim 15 in which the antigen is rheumatoid arthritis factor.

19. The process of claim 1 in which the group member is the coenzyme having at least one primary or secondary amino group per molecule.

20. The process of claim 19 in which the coenzyme is
nicotinamide-adenine dinucleotide,
nicotinamide-adenine dinucleotide phosphate,
flavin mononucleotide,
adenosine triphosphate,
flavin adenine dinucleotide, or
thiamin pyrophosphate.

21. The process of claim 1 in which the group member is an admixture of the coenzyme having at least one primary or secondary amino group per molecule.

22. The process of claim 21 in which:
(a) the coenzyme is nicotinamide-adenine dinucleotide and the enzyme is
alcohol dehydrogenase,
isocitric dehydrogenase,
α-glycerolphosphate dehydrogenase,
lactic dehydrogenase, or
glyceraldehyde-3-phosphate dehydrogenase;
(b) the coenzyme is nicotinamide-adenine dinucleotide phosphate and the enzyme is
malic enzyme,
glucose-6-phosphate dehydrogenase,
5-dehydroshikimic reductase, or
glutathione reductase;
(c) the coenzyme is flavin mononucleotide and the enzyme is
glycolic acid oxidase,
yeast cytochrome c reductase,
luciferase, or
nitro reductase;
(d) the coenzyme is adenosine triphosphate and the enzyme is glutamyl transferase,
glutathione synthetase,
glycocyamine phosphokinase,
hippuric acid synthetase, or
luciferase;
(e) the coenzyme is flavin adenine dinucleotide and the enzyme is
D-amino acid oxidase,
aldehyde oxidase,
succinic dehydrogenase,
nitrate reductase,
xanthine oxidase,
lipoyl dehydrogenase,
diaphorase,
flavin peroxidase, or
glycine oxidase; or
(f) the coenzyme is thiamin pyrophosphate and the enzyme is
carboxylase,
α-keto acid dehydrogenase, or
transketolase.

23. The process of claim 1 in which the group member is the antibiotic having at least one primary or secondary amino group per molecule.

24. The process of claim 23 in which the antibiotic is
ampicillin,
bacitracin,
colistin, or
neomycin.

25. The process of claim 1 in which the cured shaped article is a self supporting cured film.

26. The process of claim 25 in which:
(a) the resulting mixture is applied to an inert solid surface and spread thereon to form a film of the resulting mixture supported on the inert solid surface; and
(b) the film of resulting mixture is cured by exposing it to an amount of the curing agent effective for curing the resulting mixture and immobilizing the group member.

27. The cured film prepared by the process of claim 26.

28. The process of claim 26 in which the cured film is stripped from the inert solid surface.

29. The process of claim 28 in which the cured film is cut into discs after being stripped from the inert solid surface.

30. The discs prepared by the process of claim 29.

31. The process of claim 26 in which a second film of the resulting mixture is applied to the cured film and cured thereon and bonded thereto by exposing the second film to an amount of the curing agent effective for curing the resulting mixture and immobilizing the group member to increase the thickness and strength of the cured film.

32. The process of claim 26 in which a film of isocyanate-capped liquid polyurethane prepolymer is applied to the cured film and cured thereon and bonded thereto by exposing the film of isocyanate-capped liquid polyurethane prepolymer to an amount of the curing agent effective for curing the film of isocyanate-capped liquid polyurethane prepolymer to strengthen the film of immobilized group member.

33. The process of claim 32 in which the: (a) isocyanate-capped liquid polyurethane prepolymer is diluted with an inert volatile solvent before being applied to the cured film; and (b) the solvent is vaporized during curing.

34. The process of claim 26 in which: (a) the resulting mixture is admixed with an inert volatile solvent to form a solution which is applied to the inert surface; and (b) the volatile solvent is vaporized during curing.

35. The process of claim 1 in which the cured shaped article is a cured tube.

36. The process of claim 35 in which:
(a) the resulting mixture is applied to the inner surface of a pattern tube having an inner surface and an outer surface to form a film of the resulting mixture on the inner surface of the pattern tube; and
(b) the film of resulting mixture is cured by exposing it to an amount of the curing agent effective for curing the resulting mixture and immobilizing the group member to form the cured tube comprising the immobilized group member, the cured tube having an inner surface and an outer surface.

37. The process of claim 36 in which the cured tube is separated from the pattern tube.

38. The process of claim 36 in which the pattern tube is made of glass, metal, rubber, or polymer.

39. The process of claim 36 in which: (a) the resulting mixture is admixed with an inert volatile solvent to form a solution which is applied to the inner surface of the pattern tube; and (b) the volatile solvent is vaporized during curing.

40. The process of claim 36 in which a second film of resulting mixture is applied to the inner surface of the cured tube comprising the immobilized group member and cured thereon and bonded thereto by exposing the second film to an amount of the curing agent effective for curing the resulting mixture and immobilizing the group member to increase the thickness and strength of the tube comprising the immobilized group member.

41. The process of claim 36 in which a film of isocyanate-capped liquid polyurethane prepolymer is applied to the inner surface of cured tube comprising the immobilized group member and cured thereon and bonded thereto by exposing the film of isocyanate-capped liquid polyurethane prepolymer to an amount of the agent effective for curing the prepolymer to increase the strength of the tube comprising the immobilized group member.

42. The process of claim 41 in which the:
isocyanate-capped liquid polyurethane prepolymer is diluted with an inert volatile solvent before being applied to the inner surface of the tube comprising the immobilized group member; and (b) the solvent is vaporized during curing.

43. The process of claim 35 in which:
(a) the isocyanate-capped liquid polyurethane is applied to the inner surface of a first tube which is a pattern tube having an inner surface and an outer surface to form a film of the isocyanate-capped liquid polyurethane prepolymer on the inner surface of the first tube;
(b) the film of isocyanate-capped liquid polyurethane prepolymer is cured by exposing it to an amount of the curing agent effective for curing the prepolymer to form a second tube comprising cured prepolymer, the second tube having an inner surface and an outer surface;
(c) the resulting mixture is applied to the inner surface of the second tube to form a film of the resulting mixture on the inner surface of the second tube; and
(d) the film of resulting mixture is cured and bonded to the inner surface of the second tube by exposing the film of resulting mixture to an amount of the curing agent effective for curing the resulting mixture and immobilizing the group member to form a third tube comprising the immobilized group member bonded to the inner surface of the second tube.

44. The process of claim 43 in which the third tube is separated from the first tube.

45. The process of claim 43 in which the first tube is made of glass, metal, rubber, or plastic.

46. The process of claim 43 in which the isocyanate-capped liquid polyurethane prepolymer is diluted with an inert volatile solvent before being applied to the inner surface of the first tube.

47. The process of claim 46 in which the inert volatile solvent is vaporized during the curing step.

48. The process of claim 1 in which the cured shaped article is a rod comprising the immobilized group member.

49. The process of claim 48 in which:
(a) the resulting mixture is applied to the longitudinal surface of a pattern rod having a longitudinal surface and two end surfaces to form a film of the resulting mixture on the longitudinal surface; and
(b) the film of resulting mixture is cured by exposing it to an amount of the curing agent effective for curing the resulting mixture and immobilizing the group member to form a product rod comprising the pattern rod having on its longitudinal surface a coating comprising the immobilized group member.

50. The product rod prepared by the process of claim 49.

51. The process of claim 49 in which the coating comprising the immobilized group member is separated from the pattern rod to form a tube comprising the immobilized group member.

52. The tube formed by the process of claim 51.

53. The process of claim 49 in which: (a) the resulting mixture is admixed with an inert volatile solvent to form a solution which is applied to the longitudinal surface of the pattern rod; and (b) the volatile solvent is vaporized during curing.

54. The process of claim 49 in which a second film of the resulting mixture is applied to the coating comprising the immobilized group member and cured thereon and bonded thereto by exposing the second film to an amount of curing agent effective for curing the resulting mixture and immobilizing the group member to strengthen and increase the thickness of the coating comprising the immobilized group member.

55. The process of claim 49 in which a film of the isocyanate-capped liquid polyurethane prepolymer is applied to the coating comprising the immobilized group member and cured thereon and bonded thereto by exposing the film of isocyanate-capped liquid polyurethane prepolymer to an amount of curing agent effective for curing the isocyanate-capped liquid polyurethane prepolymer to strengthen the coating comprising the immobilized group member.

56. The process of claim 55 in which the coating comprising the immobilized group member with the cured prepolymer bound thereto is separated from the pattern rod to form a tube having an inner surface comprising the immobilized group member and an outer surface comprising the cured prepolymer.

57. The tube prepared by the process of claim 56.

58. The process of claim 55 in which the:
(a) isocyanate-capped liquid polyurethane prepolymer is diluted with an inert volatile solvent before being applied to the coating comprising the immobilized group member; and
(b) the solvent is vaporized during curing.

59. The process of claim 48 in which:
(a) the isocyanate-capped liquid polyurethane prepolymer is applied to a pattern rod having a longitudinal surface and two end surfaces to form a film of isocyanate-capped liquid polyurethane prepolymer on the longitudinal surface;
(b) the film of isocyanate-capped liquid polyurethane prepolymer is cured by exposing it to an amount of the curing agent effective for curing the isocyanate-capped liquid polyurethane prepolymer to form an intermediate rod comprising the pattern rod having on its longitudinal surface a first coating of cured prepolymer, the first coating having an inner surface adjacent to the longitudinal surface of the pattern rod and an outer surface; and
(c) a film of resulting mixture is applied to the outer surface of the first coating and cured thereon and bonded thereto by exposing the film of resulting mixture to an amount of the curing agent effective for curing the resulting mixture and immobilizing the group member to form a product rod comprising the pattern rod with a final coating thereon, the final coating comprising the first coating with the second coating bound thereto.

60. The product rod formed by the process of claim 59.

61. The process of claim 59 in which the final coating is separated from the pattern rod to form a tube.

62. The tube formed by the process of claim 61.

63. The process of claim 1 in which the shaped article is a cured sphere.

64. The process of claim 63 in which the sphere is formed and cured by feeding the resulting mixture dropwise into a fluid comprising the curing agent and permitting the resulting spherical drop to fall freely through the fluid.

65. The process of claim 64 in which the fluid is a liquid.

66. The process of claim 65 in which the liquid consists of the curing agent.

67. The process of claim 65 in which the liquid consists essentially of the curing agent dissolved in a solvent.

68. The process of claim 64 in which the fluid is a vapor.

69. The process of claim 68 in which the vapor consists of the curing agent.

70. The process of claim 68 in which the vapor consists essentially of a mixture of curing agent and inert gas.

71. The process of claim 64 in which: (a) the resulting mixture is admixed with an inert volatile solvent to form a solution which is fed dropwise into the fluid comprising the curing agent.

72. The process of claim 71 in which the volatile solvent is vaporized while curing the resulting mixture.

73. The process of claim 71 in which the volatile solvent is acetone, methyl ethyl ketone, methyl alcohol, ethyl alcohol, a propyl alcohol, a butyl alcohol, dimethylformamide, dimethyl sulfoxide, N-methyl-2-pyrrolidone, methylchloroform, benzene, toluene, xylene, carbon tetrachloride, chloroform, hexane, or petroleum ether.

* * * * *